(12) United States Patent
Albaugh et al.

(10) Patent No.: US 12,063,993 B2
(45) Date of Patent: *Aug. 20, 2024

(54) MATTER OF MANUFACTURE OF COMPRESSION LEGGING SYSTEM AND ASSOCIATED USES

(71) Applicant: Predictive Wear, Lafayette, IN (US)

(72) Inventors: Matthew Albaugh, Lafayette, IN (US); Pablo Argote, Lafayette, IN (US); Neal Patel, Lafayette, IN (US); Raj Patel, Lafayette, IN (US); Sriram Boppana, Lafayette, IN (US); Alexander Ocken, Lafayette, IN (US); Axel Masquelin, Lafayette, IN (US); Orlando Hoilett, Lafayette, IN (US); David Miller, Lafayette, IN (US); Michael Drakopoulos, Lafayette, IN (US)

(73) Assignee: Predictive Wear

( * ) Notice: Subject to any disclaimer, the term of this patent is extended or adjusted under 35 U.S.C. 154(b) by 0 days.

This patent is subject to a terminal disclaimer.

(21) Appl. No.: 18/309,838

(22) Filed: May 1, 2023

(65) Prior Publication Data

US 2023/0263248 A1    Aug. 24, 2023

Related U.S. Application Data

(62) Division of application No. 17/003,906, filed on Aug. 26, 2020, now Pat. No. 11,672,288.

(51) Int. Cl.
*A41D 13/12* (2006.01)
*A41D 17/02* (2006.01)
*A61B 5/00* (2006.01)
*A61B 5/0535* (2021.01)
*A61B 5/11* (2006.01)

(52) U.S. Cl.
CPC ..... *A41D 13/1281* (2013.01); *A41D 13/1254* (2013.01); *A41D 17/02* (2013.01); *A61B 5/0535* (2013.01); *A61B 5/1116* (2013.01); *A61B 5/6804* (2013.01); *A61B 5/7264* (2013.01); *A41D 2400/38* (2013.01)

(58) Field of Classification Search
None
See application file for complete search history.

(56) References Cited

U.S. PATENT DOCUMENTS

| | | |
|---|---|---|
| 7,308,294 B2 | 12/2007 | Hassonjee et al. |
| 7,474,910 B2 | 1/2009 | Hassonjee et al. |
| 7,878,030 B2 | 2/2011 | Burr |
| 7,966,052 B2 | 6/2011 | DeFusco et al. |
| 7,970,451 B2 | 6/2011 | Hassonjee et al. |
| 8,082,762 B2 | 12/2011 | Burr |
| 8,214,008 B2 | 7/2012 | Hassonjee et al. |
| 11,229,787 B2 * | 1/2022 | Daniels ............... H01B 13/00 |

(Continued)

*Primary Examiner* — Benjamin S Melhus
(74) *Attorney, Agent, or Firm* — Gutwein Law; Tyler B. Droste

(57) ABSTRACT

Described herein, is the manufacture, matter of compositions, function, methods and uses of a compression legging system that combines a swelling monitor, a patient activity monitor, medical compression legging material, and a mobile application to help PTS patients detect recurrent DVT and seek medical attention quickly before the development of PE, while reducing swelling and preventing DVT via compression therapy.

6 Claims, 28 Drawing Sheets

(56) References Cited

U.S. PATENT DOCUMENTS

| | | |
|---|---|---|
| 2009/0234262 A1 | 9/2009 | Reid, Jr. et al. |
| 2011/0060239 A1 | 3/2011 | Gaw |
| 2011/0166491 A1* | 7/2011 | Sankai ............... A41D 13/1281 |
| | | 601/84 |
| 2011/0288605 A1* | 11/2011 | Kaib .................... A61B 5/6823 |
| | | 607/5 |
| 2014/0358193 A1* | 12/2014 | Lyons ................ A61N 1/37229 |
| | | 607/48 |
| 2015/0057585 A1 | 2/2015 | Ladd |
| 2016/0135706 A1 | 5/2016 | Sullivan et al. |
| 2016/0242646 A1 | 8/2016 | Obma |
| 2016/0278642 A1 | 9/2016 | Vogel et al. |
| 2016/0324442 A1 | 11/2016 | Zdeblick |
| 2017/0196502 A1 | 7/2017 | Watson et al. |
| 2017/0196513 A1 | 7/2017 | Longinotti-Buitoni et al. |
| 2017/0354372 A1 | 12/2017 | Varadan et al. |
| 2018/0303383 A1* | 10/2018 | Connor ................... G06F 3/014 |
| 2020/0237607 A1* | 7/2020 | Ramanan ............. A61H 9/0092 |
| 2021/0251842 A1* | 8/2021 | Ramanan ............. A61H 9/0078 |

* cited by examiner

FIG. 11A

Microcontroller

Impedance Analyzing Circuit

1/2 Vdd (Vref)

Voltage Sensing multiplexers

FIG. 19 — Peak Detector

MATTER OF MANUFACTURE OF COMPRESSION LEGGING SYSTEM AND ASSOCIATED USES

CROSS REFERENCE TO RELATED APPLICATIONS

This application is a divisional from U.S. patent application Ser. No. 17/003,906 filed Aug. 20, 2020, which is a PCT Bypass continuation application of international PCT application number PCT/US20/20871, filed Mar. 4, 2020 which claimed benefit of U.S. provisional application No. 62/813,887, filed Mar. 5, 2019, the subject matter of each of the above referenced disclosures is expressly incorporated by reference herein.
  a PCT international patent application of and claims the priority of U.S. provisional patent application Ser. No. 62/856,410, titled "IMPEDANCE BASED COMPRESSION LEGGING SYSTEM" filed on Jun. 3, 2019, U.S. provisional patent application Ser. No. 62/813,887, titled "COMPRESSION LEGGING SYSTEM" filed on Mar. 5, 2019 and incorporates the subject matter of each thereof in its entirety.

This application incorporates the subject matter of U.S. provisional patent application Ser. No. 62/405,442 filed on Oct. 7, 2016, in its entirety.

FIELD OF THE INVENTION

The present disclosure relates to the matter of construction and use of a compression legging system that combines an impedance monitor, a patient activity monitor, medical compression legging material, and a mobile application for detection of recurrent disease. The compression legging system is intended for the detection of human diseases including a group of congestive heart failure (CHF), post-thrombotic syndrome (PTS), deep vein thrombosis (DVT), venous injury, venous stasis (Virchow's triad of hypercoagulability), pulmonary emboli (PE), inflammation and swelling of the extremities.

FEDERALLY SPONSORED RESEARCH OR DEVELOPMENT

Not applicable.

SEQUENCE LISTING, A TABLE, OR A COMPUTER PROGRAM

Not applicable.

BACKGROUND

Post-thrombotic syndrome (PTS) affects 750,000 individuals in the U.S. and develops after deep vein thrombosis (DVT damages valves in the deep venous system. History of DVT, venous injury, and venous stasis (Virchow's triad of hypercoagulability) place PTC patients at high risk of recurrent DVT and pulmonary emboli (PE) (cumulative incidence of recurrent DVT in this population is approximately 20%).

Symptomatic DVT accounts for most PE, and if not treated within three months, has a 15% mortality rate. This mortality rate can be reduced to 4% if the DVT is detected successfully at an earlier stage. Therefore, detection of symptomatic, recurrent DVT in PTS patients may allow for treatment-based reduction in the fatality caused by PE in this population.

PTS patients are commonly prescribed compression stockings to prevent recurrent DVT, prevent venous ulceration, and reduce leg swelling. Compression stockings, compression leggings, and compression sleeves are produced by many manufacturers. These compression garments can be outfitted with several textile-based electrodes, for example textile electrodes for electrocardiogram (EKG) monitoring created by Textronix, Inc. Several commercially-available bio-impedance body monitors perform similar measurements and analyses of hydration and similar body properties. These include monitors sold by Tanita Corporation, for example Ironman Body Composition Monitors, InpediMed for example SOZO system which has been FDA-cleared for detection of lymphedema, and InBody USA, for example InBody 770, marketed for detection of lymphedema.

The Wells Criteria are a well-established clinical assessment that determines the likelihood that a patient has DVT, where the likelihood of DVT correlates linearly with a patient's Wells Score.

TABLE 1

Wells Criteria for the likelihood of DVT: A patient's Wells Score is the sum of their scores for each Wells Criterion. −2 to 0: Low probability; 1 to 2 points: Moderate probability; 3 to 8 points: High probability [34]. "Given" - all PTS patients have a history of DVT.

| Wells Criterion | Score | Proposed Method |
|---|---|---|
| Active cancer (within past 6 months) | 1 | Section 3.2.4 |
| Paralysis, paresis, or recent cast immobilization | 1 | Section 3.2.2 & 3.2.4 |
| Recently bedridden for 3+ days or major surgery w/in 12 weeks | 1 | Section 3.2.2 & 3.2.4 |
| Localized tenderness | 1 | Section 3.2.4 |
| Entire leg swelling | 1 | Section 3.2.1 |
| Calf swelling at least 3 cm larger than asymptomatic leg | 1 | Section 3.2.1 |
| Pitting edema confined to symptomatic leg | 1 | Section 3.2.4 |
| Collateral superficial veins (non-varicose) | 1 | Section 3.2.4 |
| Previous documented DVT | 1 | Given |
| Alternative diagnosis at least as likely as DVT | −2 | Section 3.2.4 |

A Wells Score of <1 rules out DVT with a sensitivity and negative predictive value of 100%. Overall, the Wells Score can predict DVT with a sensitivity of 77%-98%, a specificity of 37%-58%, a negative predictive value of 81-98%, and a positive predictive value of 14.2-63%, making the criteria a robust determination of patient DVT.

As patients with PTS are at high risk for recurrent DVT, and recurrent DVT is in turn an important risk factor for fatal PE, it is critical that PTS patients quickly recognize recurrent DVT and seek medical attention.

Bio-impedance spectroscopy (BIS) is a well-established, reliable method to determine the level of swelling in a segment of tissue. It gives 96%-100% sensitivity and 96% specificity in detecting a variety of clinical manifestations of swelling and outperforms circumferential and volumetric leg measurements in sensitivity and specificity. BIS works by injecting multiple frequencies of alternating current (AC) into a volume of tissue and measuring the impedance of the tissue at each frequency.

Accumulation of fluid in tissue, such as in PTS-induced swelling, alters the tissue's impedance spectrum and can therefore be detected with BIS. In the tetrapolar electrode configuration (TEC), four electrodes are used for BIS: two current-injecting electrodes and two voltage-sensing electrodes. TEC minimizes the impact of variable skin-electrode contact impedances, polarization effects, and movement artifacts, since the voltage-sensing electrodes draw negligible current.

BRIEF SUMMARY OF THE INVENTION

The present disclosure comprises a compression legging system that combines a swelling monitor, a patient activity monitor, a medical compression legging, and a mobile application. The compression legging system intended to help patients detect recurrent DVT (and associated symptoms) to seek medical attention prior to the development of PE. The application of the compression legging system will simultaneously reduce swelling and prevent DVT via compression therapy.

The proposed methodology is the first attempt to bring scientifically-validated clinical evaluations of DVT to the home environment. Rather than mandating patients return to the clinic for re-evaluation when they subjectively suspect recurrent DVT, the proposed smart compression legging and accompanying mobile application may utilize a well-established, objective, and scientifically-validated clinical evaluation (the Wells Score) to determine the likelihood that a patient has developed DVT. The system does not require a compression user to locate and use a separate impedance-measuring device to track their impedance and derived measurements. The system does not require a physician or other person to meet with the user to take impedance measurements or to view impedance measurements or derivative measurements. Consequently, this strategy has potential to substantially reduce the incidence and mortality of PE in the PTS patient population.

The proposed smart compression legging and paired mobile application may utilize a combination of non-invasive sensors and user-answered questions to generate a Wells Score for each patient. PTS patients must differentiate between recurrent DVT and the non-DVT-associated episodic and chronic pain and swelling they often experience. PTS patients are generally told to rest and elevate their legs for 24 hours before seeking medical care for leg pain and swelling. If elevation does not reduce these symptoms, the patient is then screened for DVT. Consequently, if a patient receives a moderate or high Wells Score, the proposed device may notify the patient via the mobile app that they should carefully monitor, elevate, and rest their leg for the next 24 hours. The proposed device may then analyze the patient's Wells Score during such elevation and may prompt the patient to seek medical care for potential DVT if no improvement occurs within 24 hours. In this manner, the proposed smart compression legging may help PTS patients detect recurrent DVT through a well-established clinical evaluation and seek medical attention quickly before the development of PE while simultaneously reducing swelling and preventing DVT via compression prophylaxis.

In illustrative embodiments, the present invention comprises a compression garment, a wearable sensor network, and an application. Examples of detailed applications are described below.

In illustrative embodiments, the present invention discloses the manufacture of a compression legging system.

In a further aspect of the disclosure, use of a compression legging system to help PTS patients detect recurrent DVT.

In a further aspect of the disclosure, the compression legging system may be adapted for use of detecting diseases other than PTS, such as congestive heart failure, and lymphedema, as well as post-operative care.

In a further aspect of the disclosure, the legging's ability to aid in the detection of DVT, lower cost, and design considerations for comfort, aesthetic, and ease of use make it significantly superior to all competitors.

BRIEF DESCRIPTION OF THE DRAWINGS

FIG. 11A illustrates a microcontroller.

DETAILED DESCRIPTION OF THE INVENTION

The present disclosure relates to, inter alia, a novel compression legging system which functions as a real-time bio-impedance and activity monitor for detection of swelling in the extremities relevant to several human diseases. Likewise, methods for manufacture and utility of such a compression legging system in the detection and/or prevention of human disease conditions are disclosed herein. The embodiments disclosed herein are not intended to be exhaustive.

The definitions of certain terms as used in this specification are provided below. Unless defined otherwise, all technical and scientific terms used herein generally have the same meaning as commonly understood by one of ordinary skill in the art to which this invention belongs. As used in this specification and the appended claims, the singular forms "a", "an" and "the" include plural referents unless the content clearly dictates otherwise. For example, reference to "a system" includes a combination of two or more components herein, and the like.

Terminology

As used herein, "real-time" refers to the period describing the use of the compression system—i.e. while worn.

As used herein, "computation time" refers to the ability of the compression system hardware to collect, analyze, and transmit information within real-time.

As used herein, "classification accuracy" refers to the ability of the compression system hardware described to collect, analyze, segment, and transmit information concerning specific movements of an individual while wearing the compression system.

As used herein, "segmentation accuracy" refers to the accuracy of the compression system hardware to detect, extract, and transmit various movements within a signal.

Overview

The disclosed system comprises a combination of three functional components: a compression garment, a wearable sensor network, and an application. A compression garment could be any skin-contacting, or near-skin, garment (e.g. waist high stockings, knee high stockings, pantyhose, compression sleeve, headband). In illustrative embodiments described herein, the present disclosure refers to the use of a compression system applied to the leg, but this device could be utilized on the arm or any other portion of the body where these garments could be worn.

The disclosed system utilizes dry textile electrodes for tetrapolar electrode configuration (TEC). These electrodes are applied to the skin at a pressure of 15-40 mmHg, which is known to significantly decrease skin-electrode contact impedance.

Figure 1:
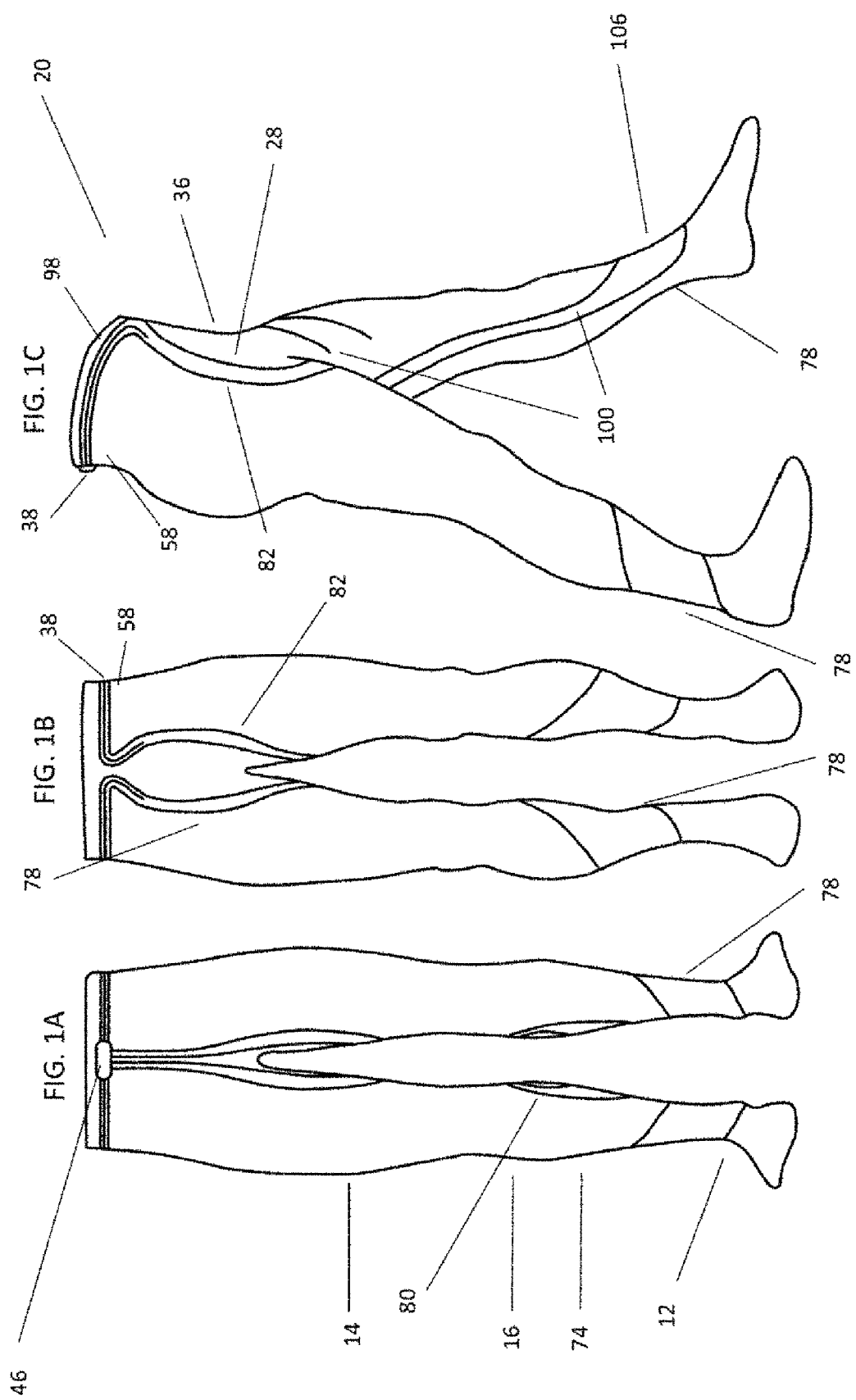
FIG. 1A illustrates a back view of the smart compression legging system that comprises compression material containing the following components: i) compression material with fabric traces, ii) central hardware housing the monitor, iii) current-injecting electrodes, and iv) voltage sensing electrodes. Features of exterior are shown; fabric traces and the central hardware housing the monitor.
FIG. 1B illustrates a front view of the smart compression legging system that comprises compression material containing the following components: i) compression material with fabric traces, ii) central hardware housing the monitor, iii) current-injecting electrodes, and iv) voltage sensing electrodes. Features of exterior are shown; fabric traces and the central hardware housing the monitor.
FIG. 1C illustrates a side view of the smart compression legging system that comprises compression material containing the following components: i) compression material with fabric traces, ii) central hardware housing the monitor, iii) current-injecting electrodes, and iv) voltage sensing electrodes. Features of exterior are shown; fabric traces and the central hardware housing the monitor.

The system in the smart compression legging is depicted in FIG. 1. A circular current-injecting band electrode 80 lies on each ankle 12 and each upper thigh 14. Five voltage-sensing electrodes 78 lie on each leg 16 between each pair of current-injecting band electrodes 78. A multiplexor may sequentially alternate which pair of voltage-sensing electrodes 80 is activated to enable segmental impedance analysis of each leg 16. This monitor may also detect swelling of the entire leg according to the Wells Criterion Scoring (Table 1).

As used herein, the term "composition" refers to a product with specified ingredients in the specified amounts, as well as any product which results, directly or indirectly, from combination of the specified ingredients in the specified amounts.

Figure 4:
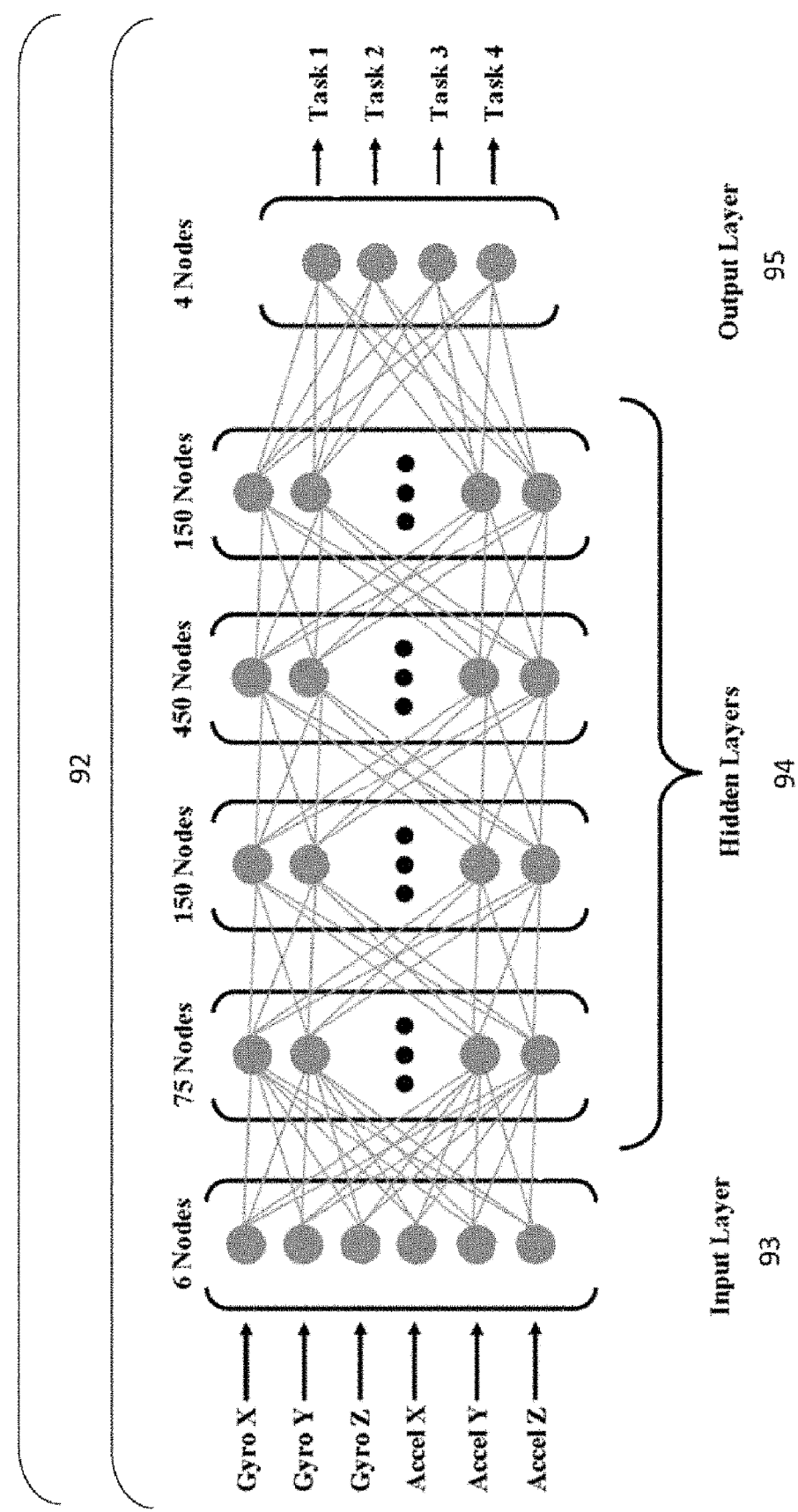
FIG. 4 illustrates a linear neural network that could be utilized to classify four tasks: 1) standing, 2) sitting, 3) sleeping, and 4) elevating the leg. Accel is accelerometer. Gyro is gyroscope.

The system 20 can take bio-impedance measurements in real-time, while a user 22 (FIG. 7) performs activities. The system 20 does not require a user 22 to remain unmoving. This is the result of the incorporation of accelerometer ("accel")-gyroscope ("gyro") units into the system. The system 20 uses accelerometers 24 and an artificial neural network (ANN) 26 to distinguish between several classes of clinically-relevant patient activity, including sitting, standing, sleeping and elevating the leg (FIG. 4). An ANN is created to accurately detect and classify five simple movement and three complex movements using data from five AGMs on the wearable sensor network (WSN) 28. To achieve this, a Recurrent Neural Network (RNN) 30 may be utilized (see FIG. 8). RNNs 30 have shown promising performances in areas such as speech recognition, label generation, handwriting recognition, and language modeling. In recent years, RNNs 30 have been utilized successfully to classify many complex and simple tasks such as running, sitting, standing, jumping, and walking left, right, forwards, and backwards with accuracies exceeding 90%. This accuracy is commonly attributed to RNNs 30 ability to exploit contextual and temporal information within variable length signals. In this manner, the proposed RNN 30 may be able to detect the larger context of a task, such as how a user 22 repetitively swings their arms while running. Using all 30 individual signals (6 samples from each of the 5 SUs 32) as input, the RNN 30 may classify across a 5 second snapshots in time. This methodology may allow the passing window to observe the activity of a user 22 within a larger frame of reference. The network 34 developed may be evaluated across three metrics:

To properly evaluate potential RNNs 30, the networks 34 may be trained and evaluated using open source datasets, such as the University of Southern California human activity dataset (USC-HAD). Multiple architectures, such as Long Short-Term Memory Deep Recurrent Neural Networks (LSTM-DRNN) and LSTM Convolutional neural networks (LSTM CNN) may be evaluated.

The wearable sensor network (WSN) 28 comprises the circuitry utilized to provide the functionality of the smart compression garment 36 and the enclosures 38 utilized to join the sensors 40 to the smart compression garment 36. The circuitry of the WSN 28 comprises an accelerometer-gyroscope module network (AGMN) 42, bio-impedance module 44, and a central hardware unit 46.

The AGMN 42 comprises three accelerometer-gyroscope modules 42 located on the garment 36. For the legging form factor of the smart compression garment 36, these are placed on each upper thigh 14 and the lower back 50. These modules 42 are a small electromechanical device that measures static and dynamic acceleration forces. These sensors 42 are highly sensitive and commonly used in missiles, cell phones, and other devices to determine the orientation of the device in three-dimensional space. The data collected from these modules may be utilized to classify the activity of the user 22 (e.g. walking, sitting, running, standing, sleeping, elevating the extremity, and others). In addition, this data is utilized to select times to collect impedance measurements from the user. Each of these sensors 42 may be encased in an enclosure, for example a small plastic enclosure made via injection molding. The water-resistant enclosure may protect the device from damage due to abrasion, impact, or water. These enclosures may be attached to the compression garment 36 via hook and loop fastener such as Velcro®, a clip, or some other fastener which may allow the enclosure to be removed and replaced. The accelerometer-gyroscope modules' enclosures could potentially be left out without compromising their function, and thus without compromising the function of the device 20.

Each accelerometer-gyroscope module 42 may be connected to the central hardware 46. This may be accomplished via traditional wiring, textile electronic traces or conductive connections. The central hardware may therefore collect all data from the AGMN 42 and may power the AGMN 42. Instead of using accelerometer gyroscope units, other means of monitoring orientation of the device could be used, for example magnetometers or any combination of accelerometers, magnetometers, and gyroscopes. Instead of using only three accelerometer gyroscope units, more or fewer units could be utilized in the wearable sensor network.

Figure 9:
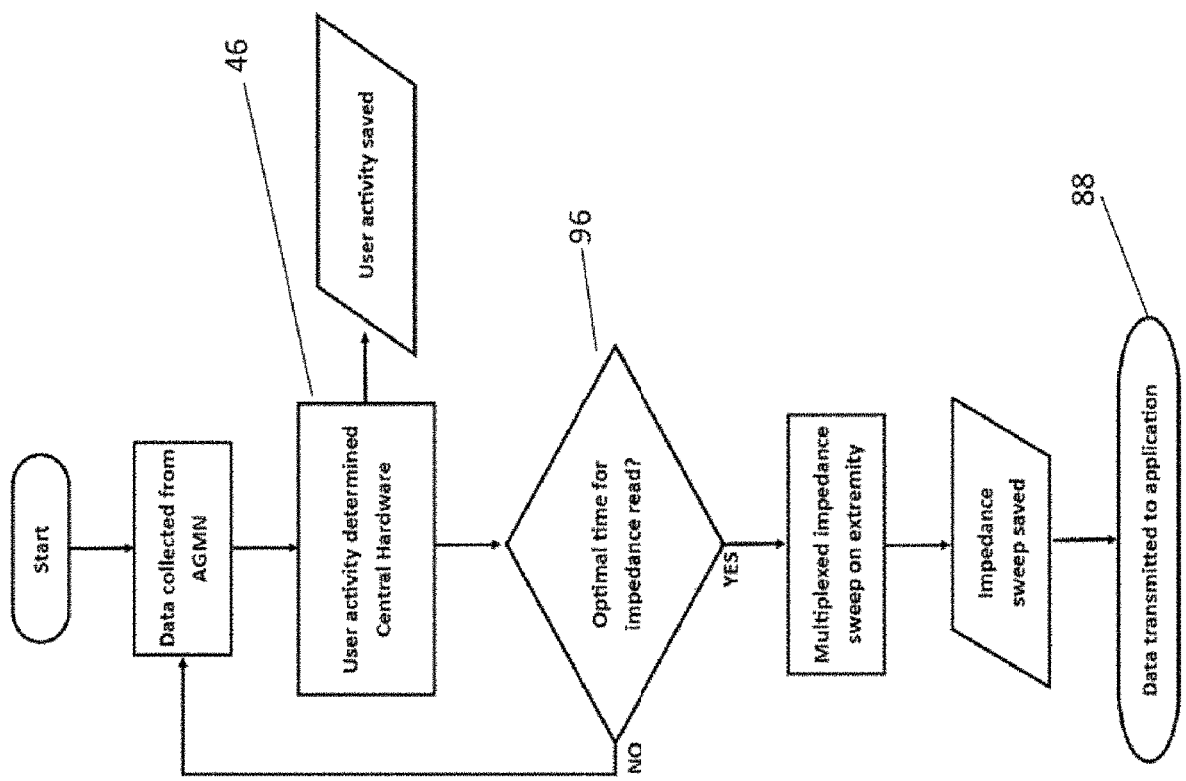
FIG. 9 illustrates the central hardware flowchart. Impedance and user activity are saved and transmitted to the mobile application device.
Figure 10:
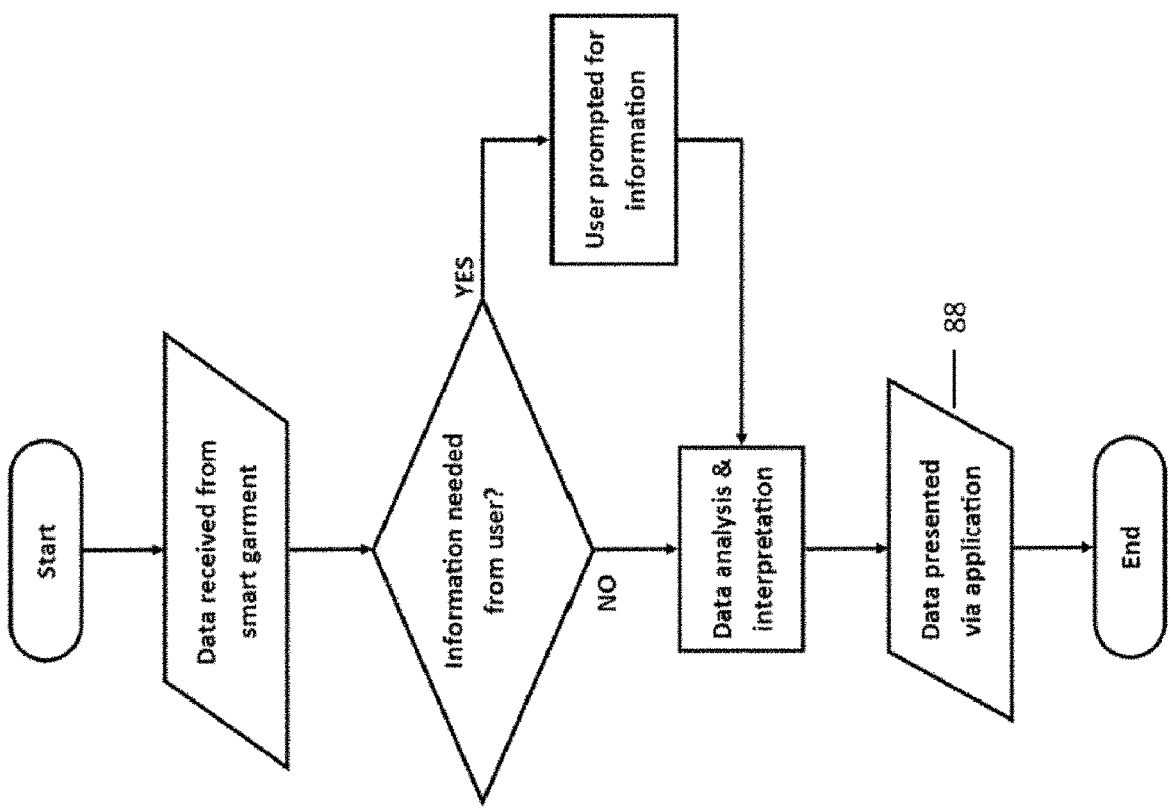
FIG. 10 illustrates the mobile application flowchart.
Figure 11B:
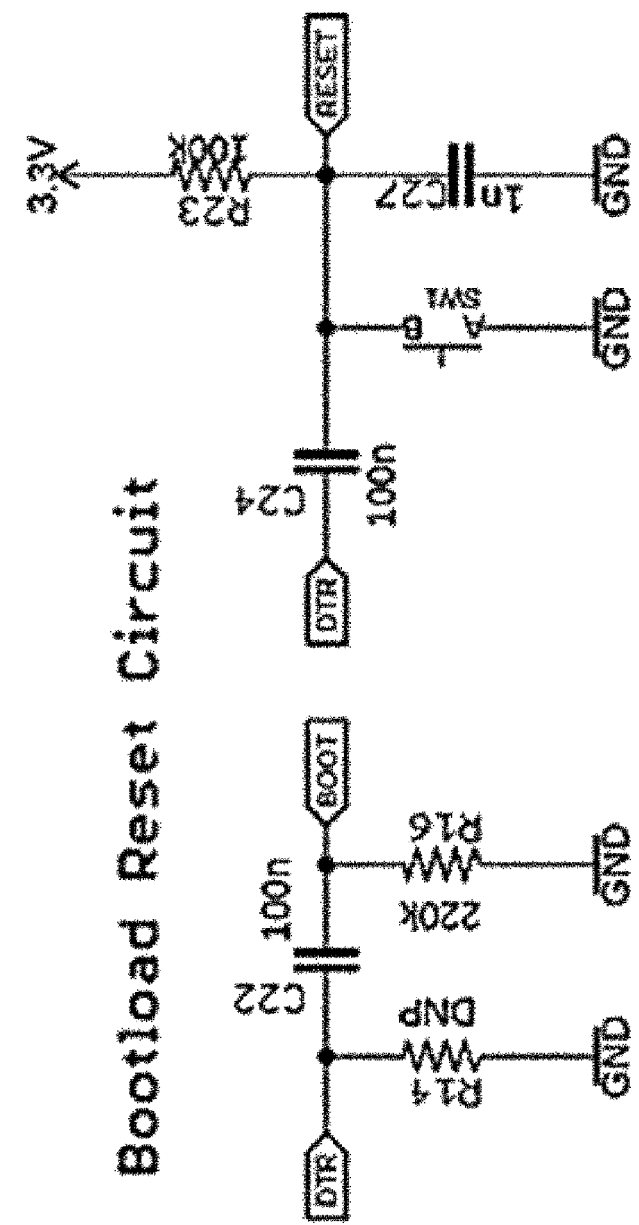
FIG. 11B illustrates a bootload reset circuit.
Figure 11C:
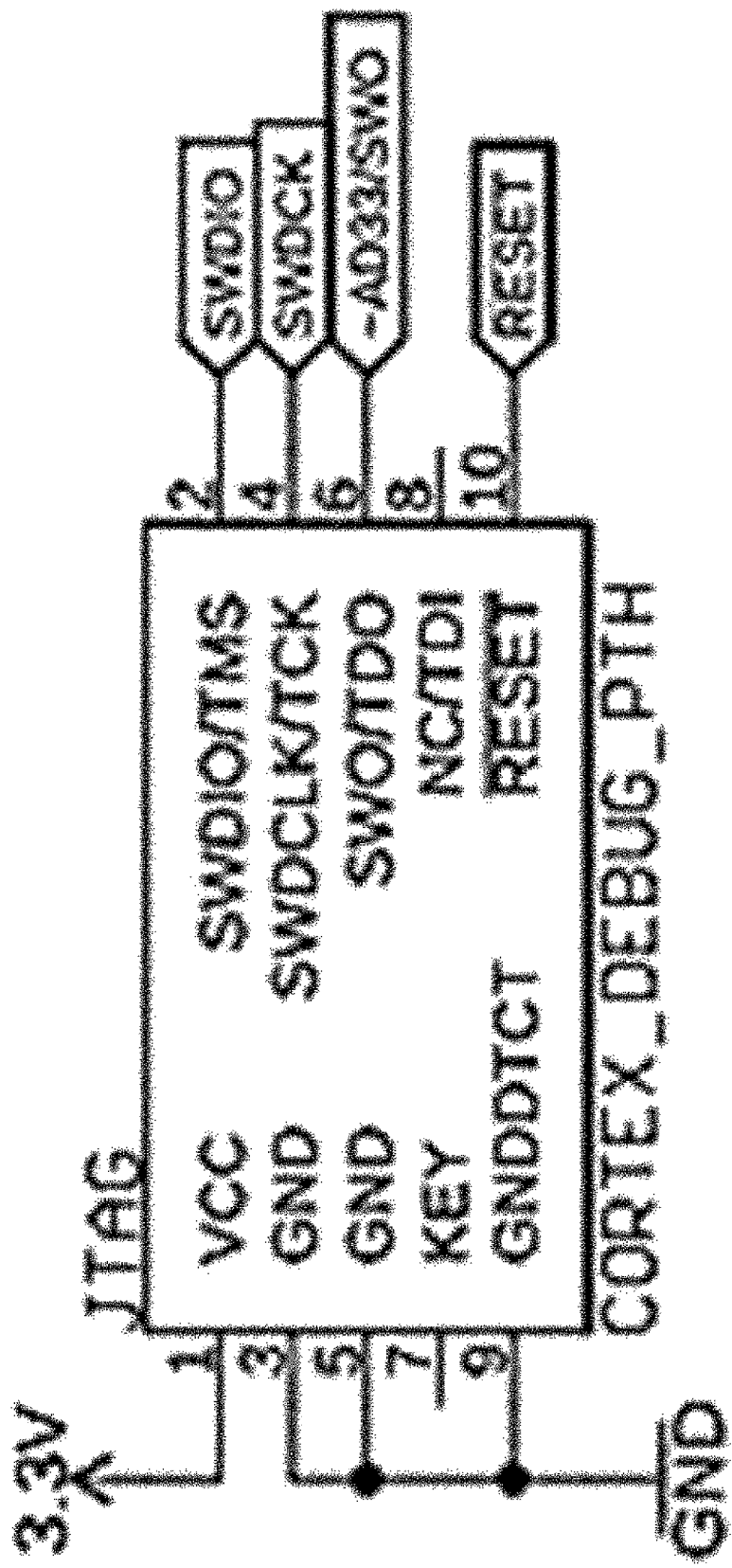
FIG. 11C illustrates a Joint Test Action Group (JTAG) interface.
Figure 12:
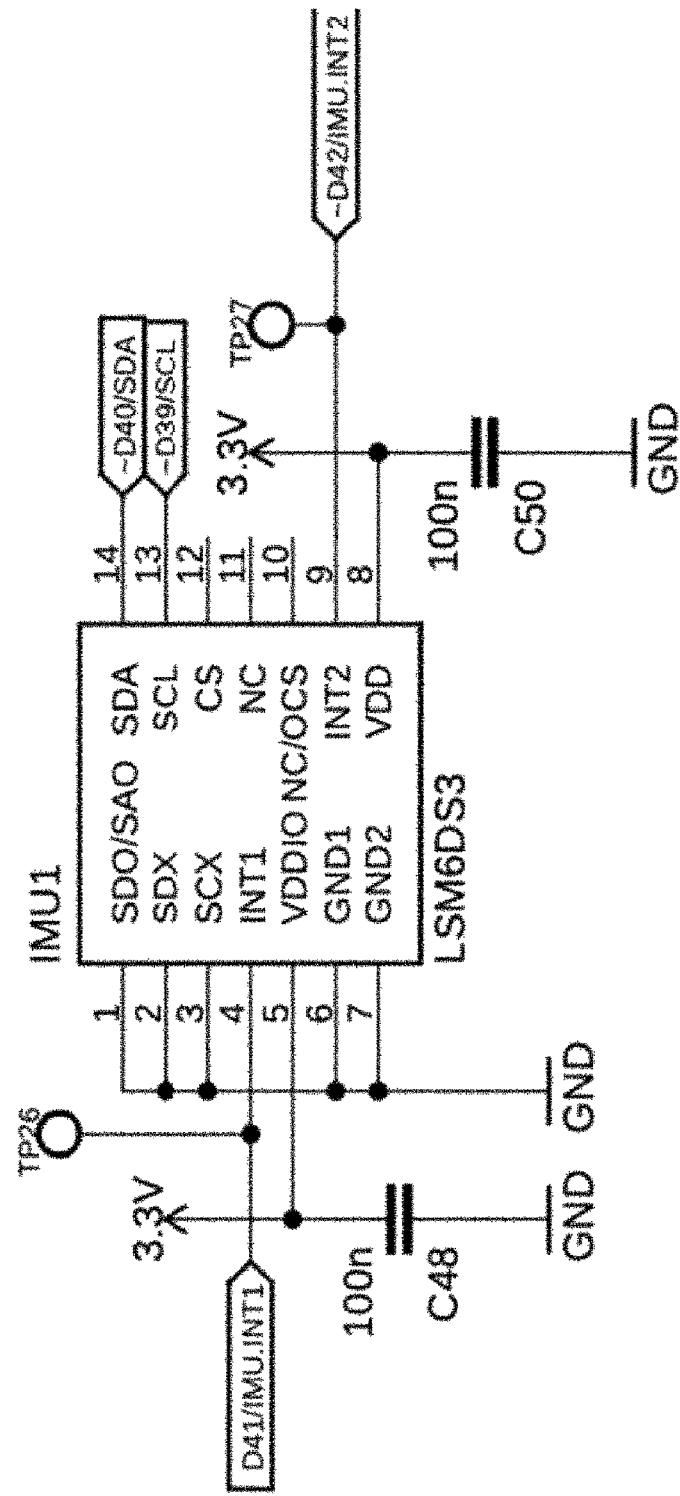
FIG. 12 illustrates an accelerator or gyroscope.
Figure 13A:
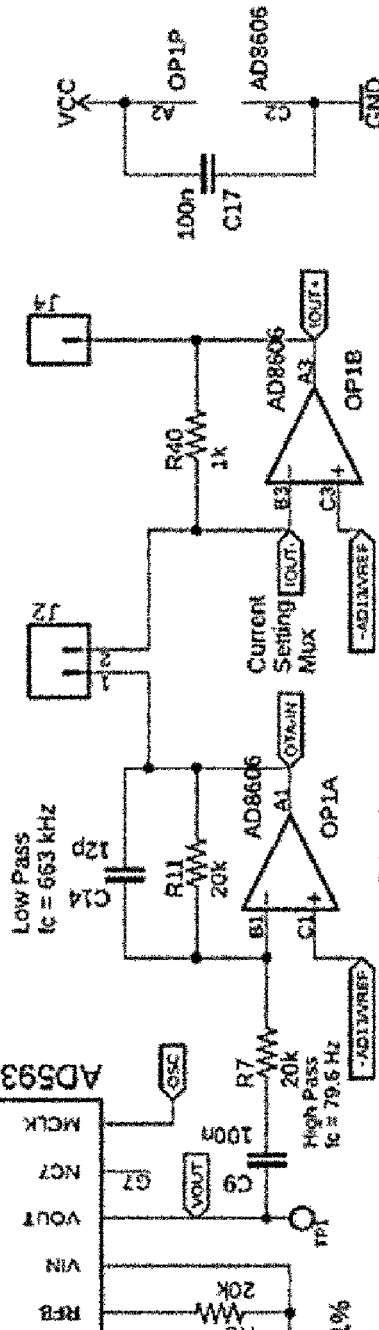
FIG. 13A illustrates an impedance analyzing circuit.
Figure 13B:
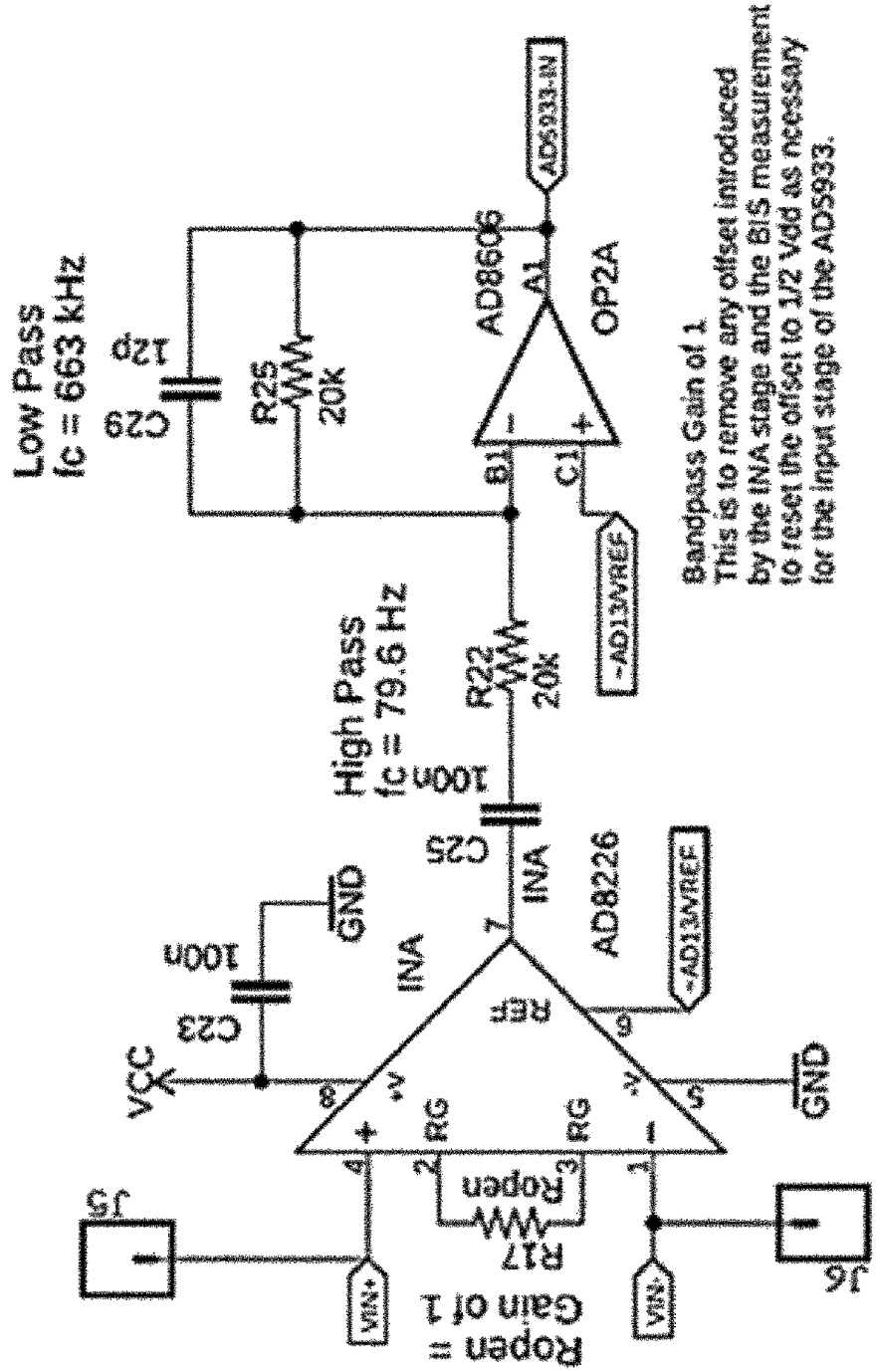
FIG. 13B illustrates an impedance analyzing circuit and biopotential measurement and filter.
Figure 14A:
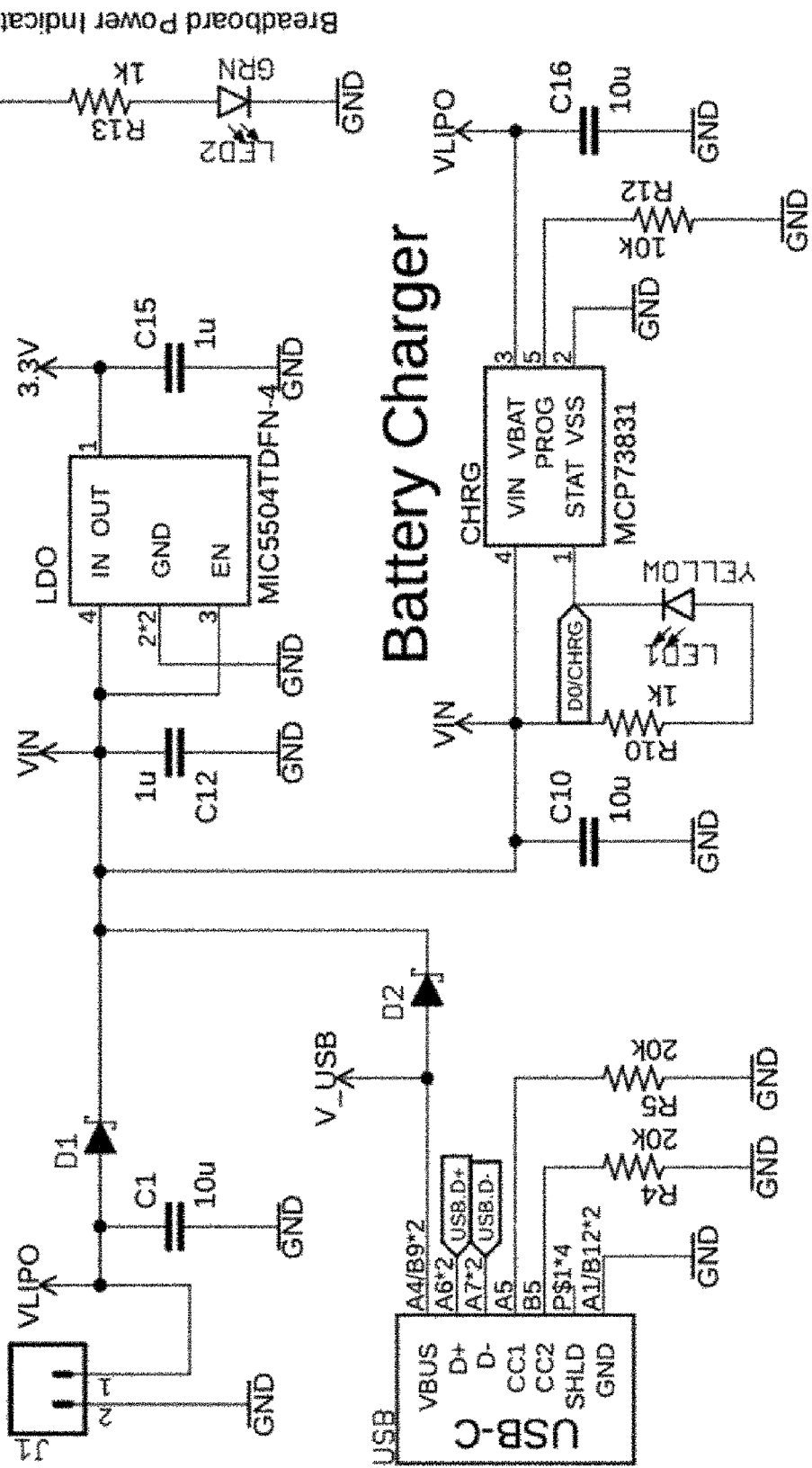
FIG. 14A illustrates an on/off switch, voltage regulator and battery charger.
Figure 14B:
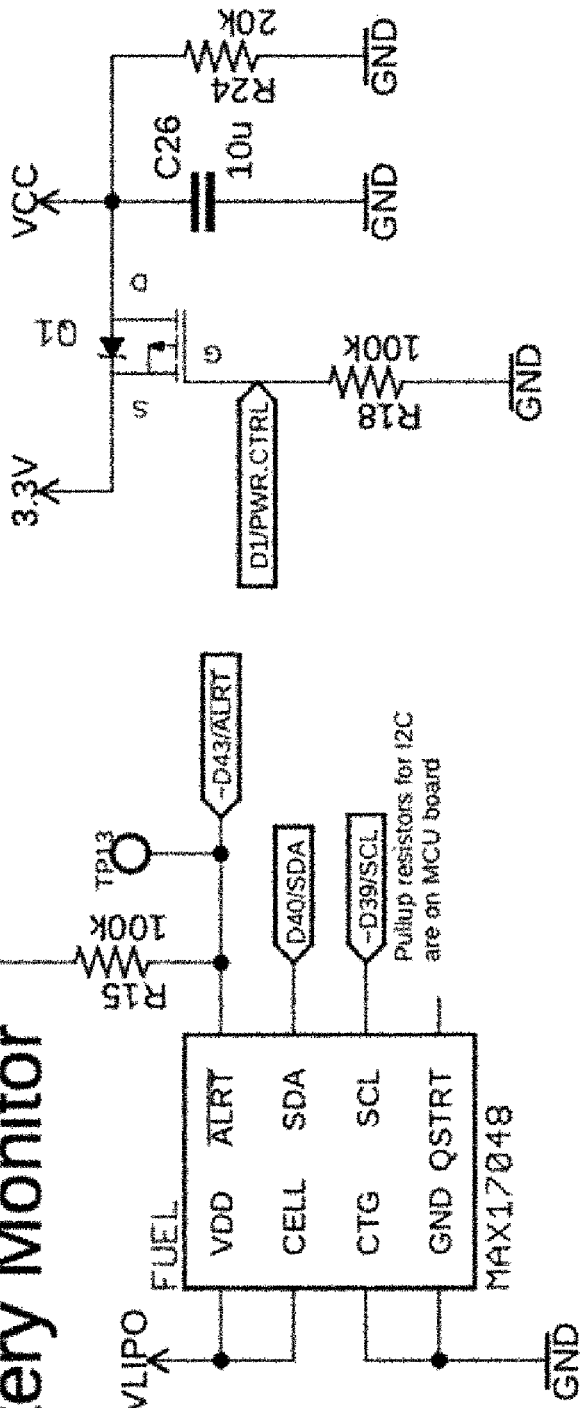
FIG. 14B illustrates a battery monitor and power switch.
Figure 14C:
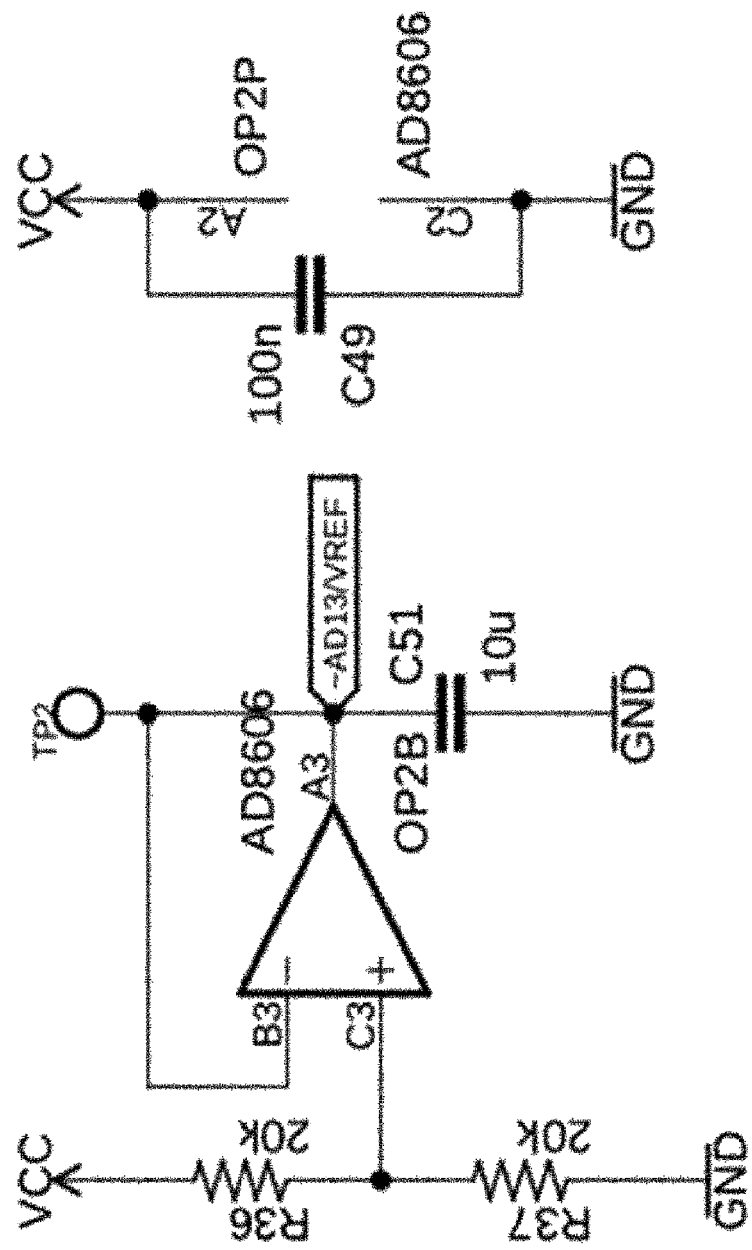
FIG. 14C illustrates a voltage supply (Vdd) and voltage reference (Vref).
Figure 15A:
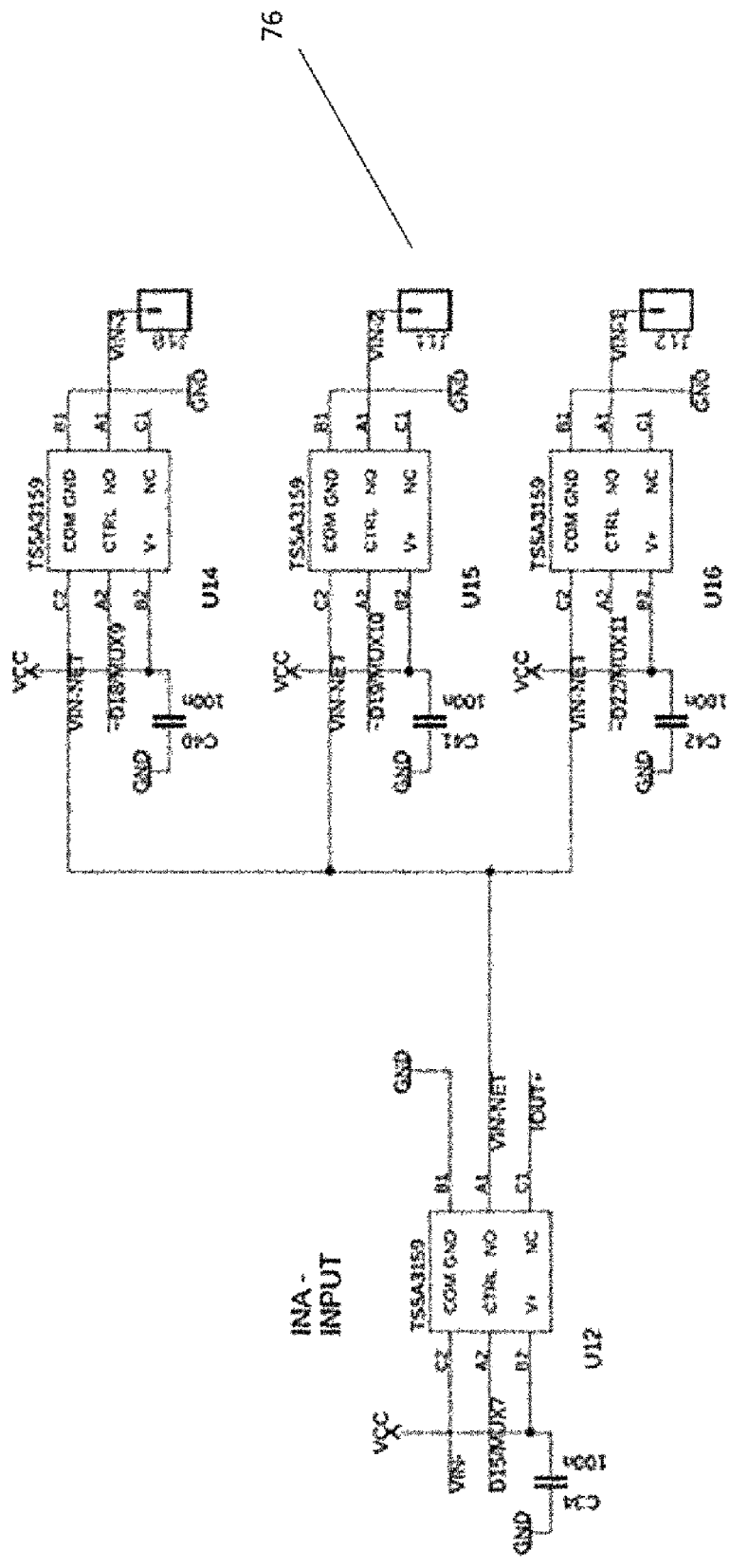
FIG. 15A illustrates a voltage sensing multiplexer.
Figure 15B:
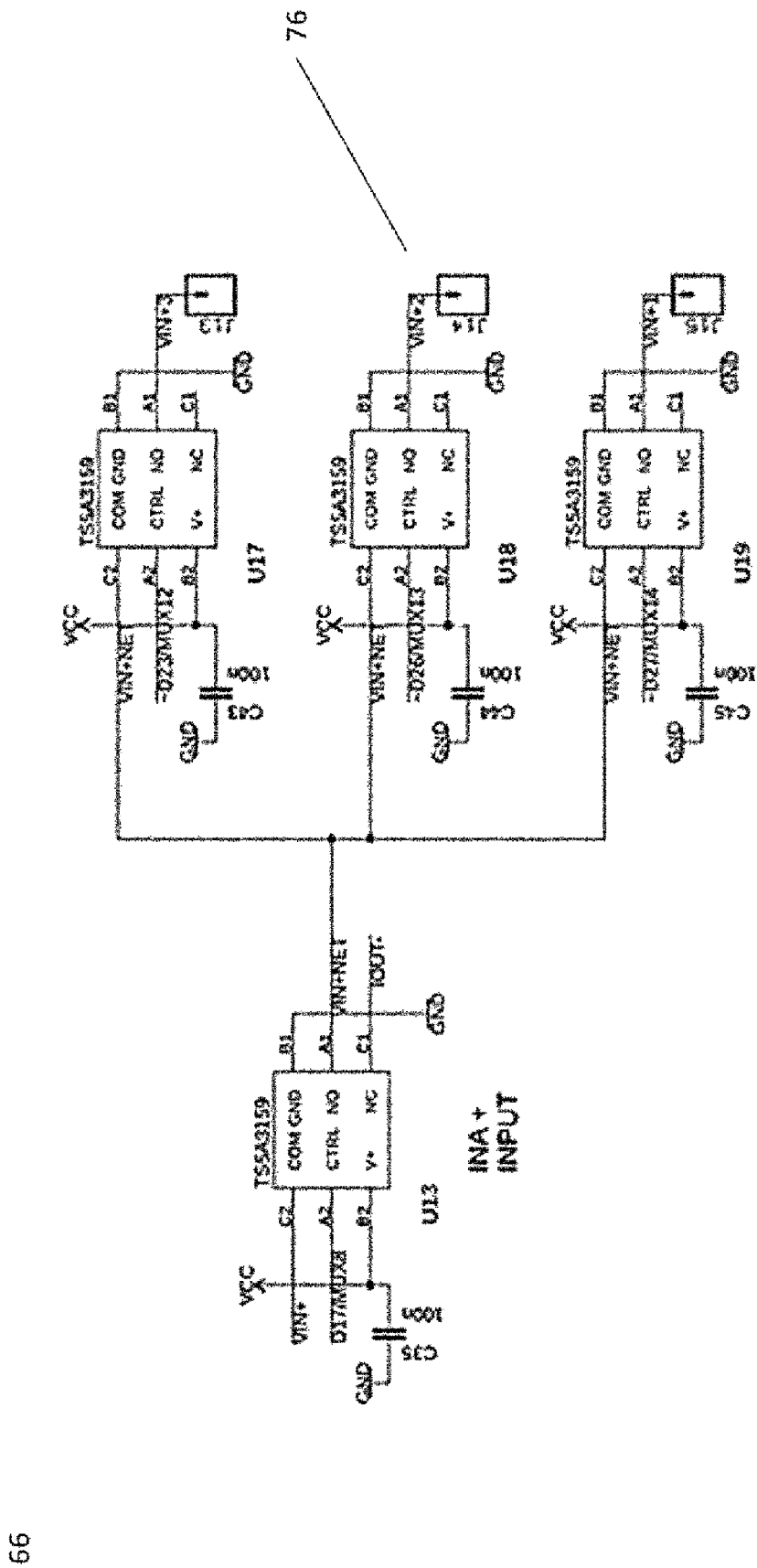
FIG. 15B illustrates a voltage sensing multiplexer.
Figure 16:
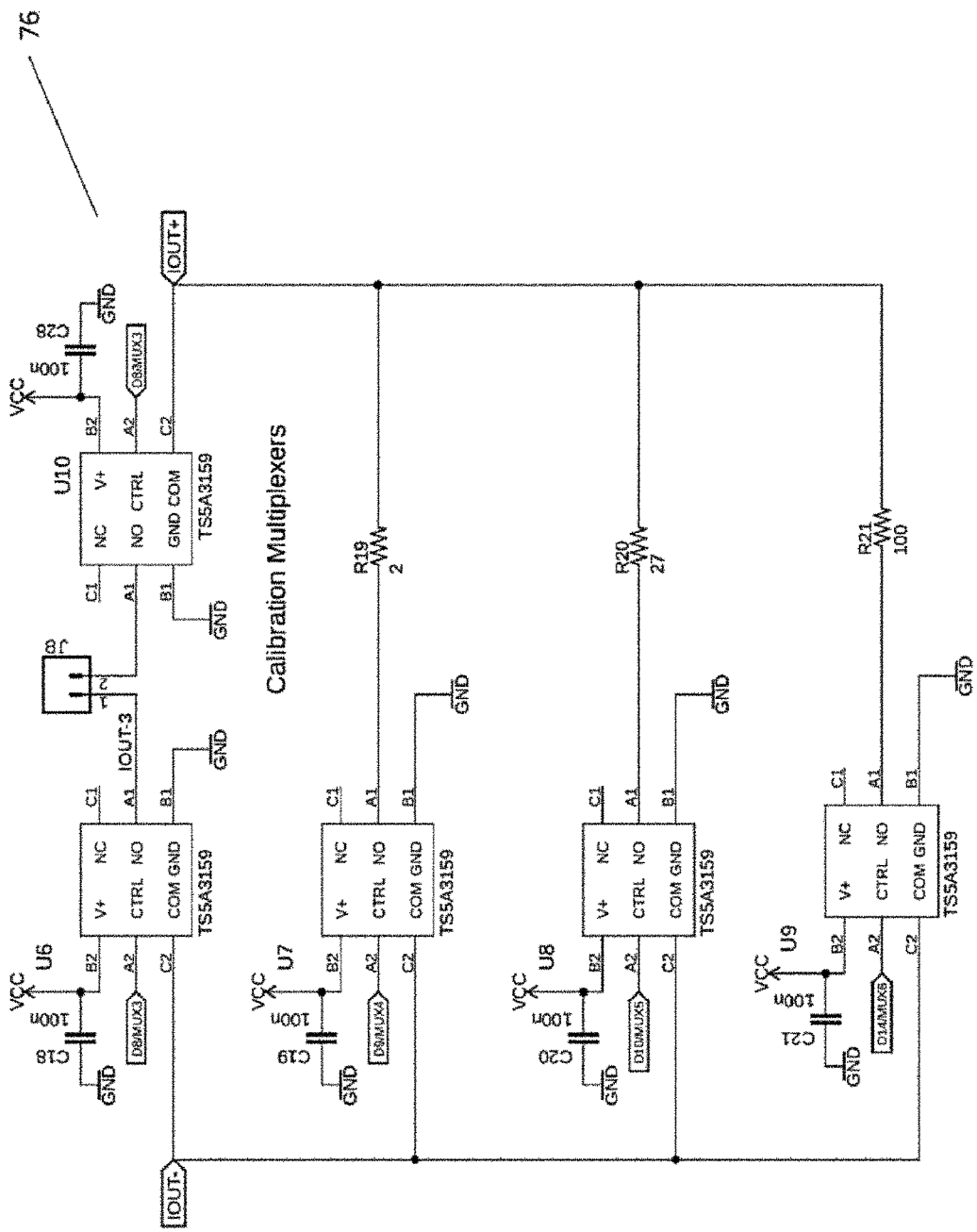
FIG. 16 illustrates a band injecting multiplexer.
Figure 17:
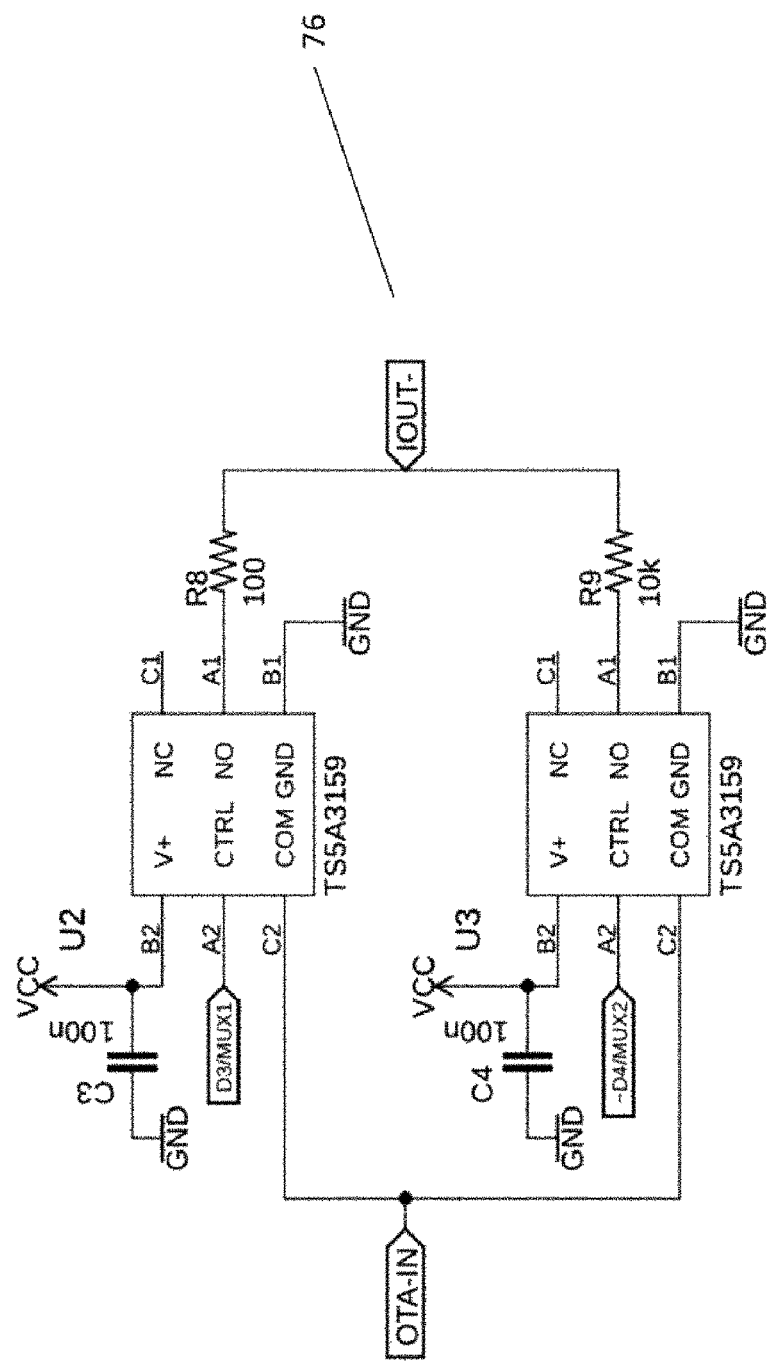
FIG. 17 illustrates a current sensing multiplexer.
Figure 18:
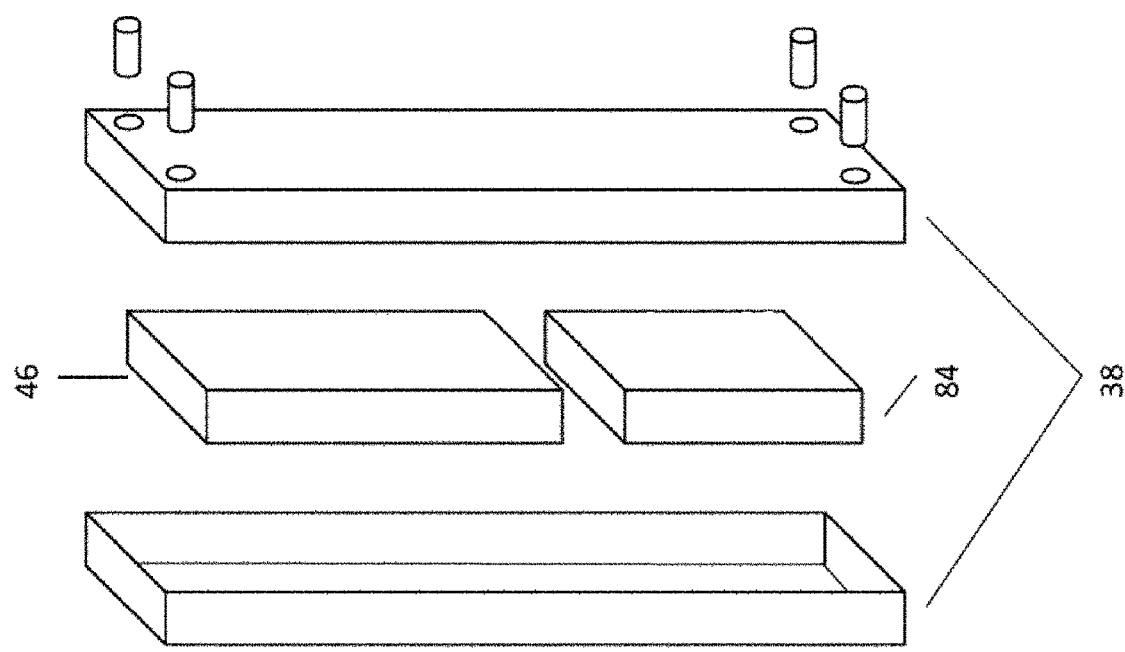
FIG. 18 illustrates central hardware with battery in an enclosure.
Figure 19:
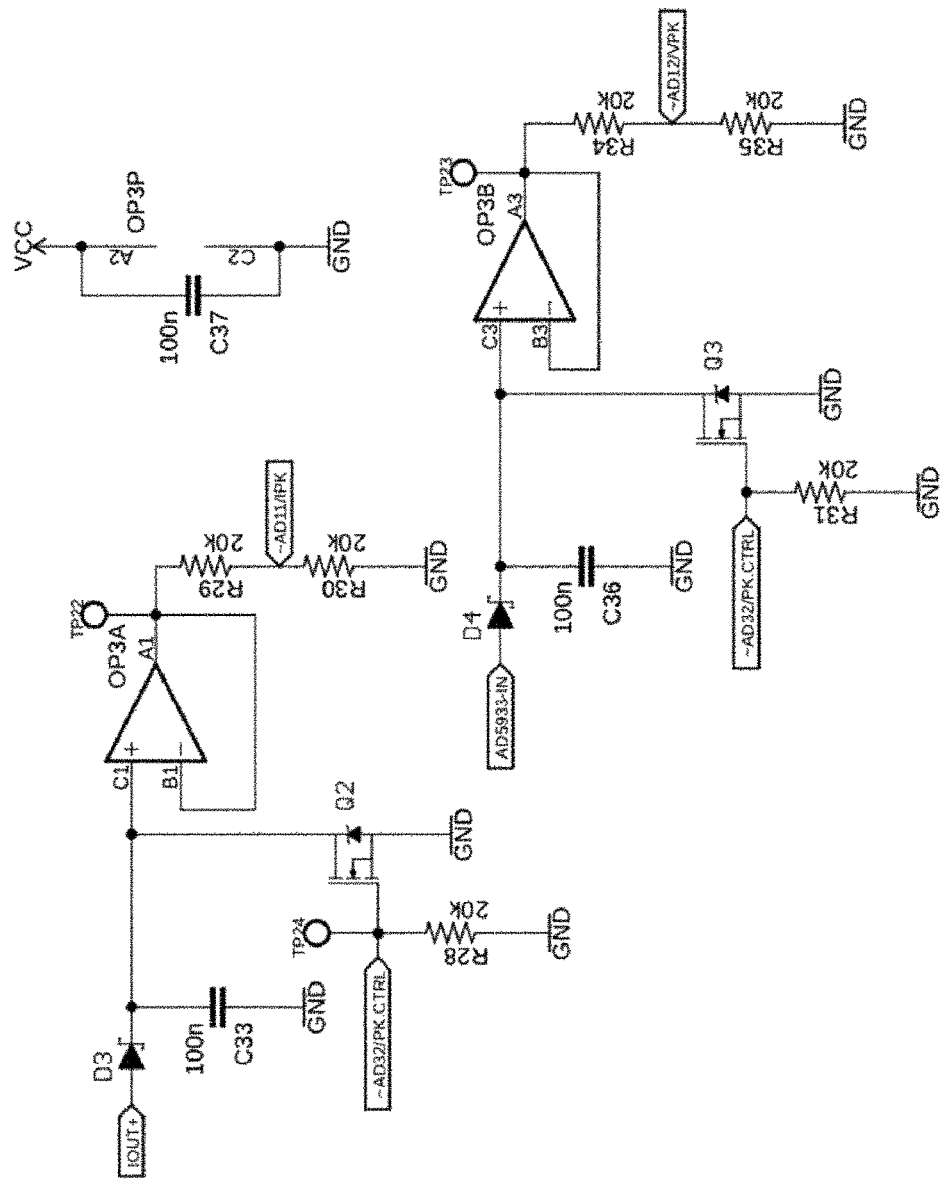
FIG. 19 illustrates a peak detector.
Figure 20:
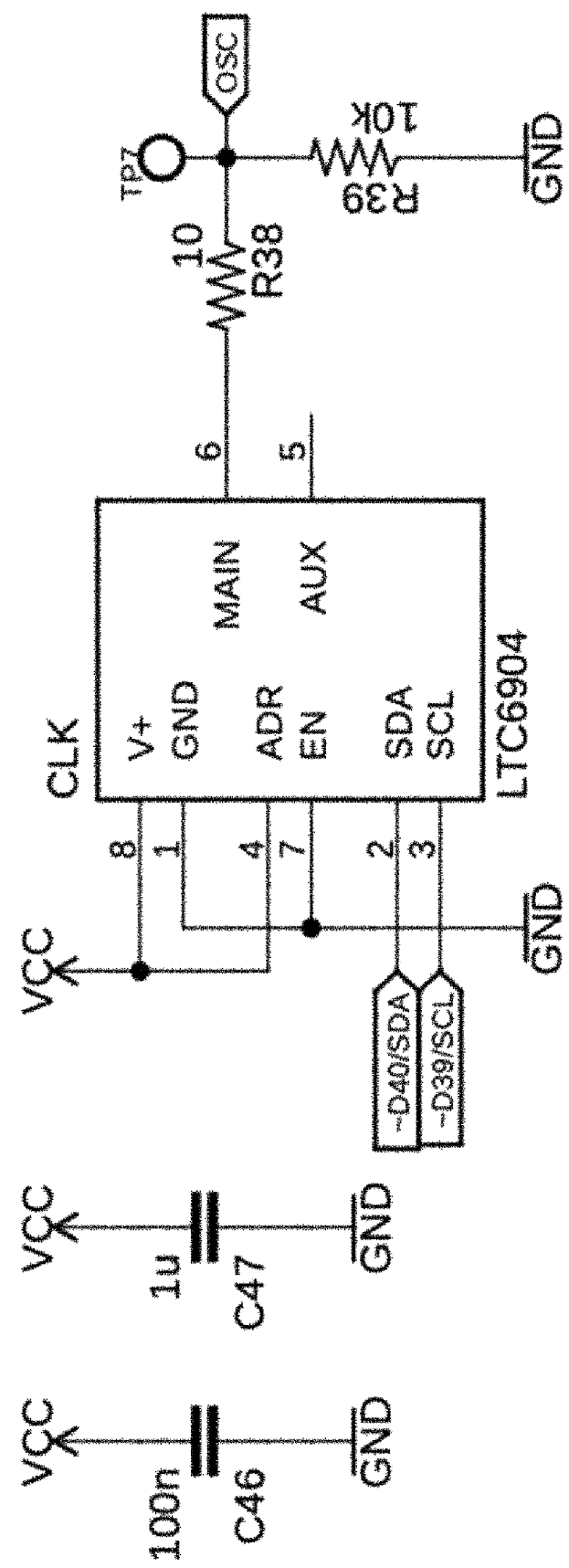
FIG. 20 illustrates a clock.
Figure 21:
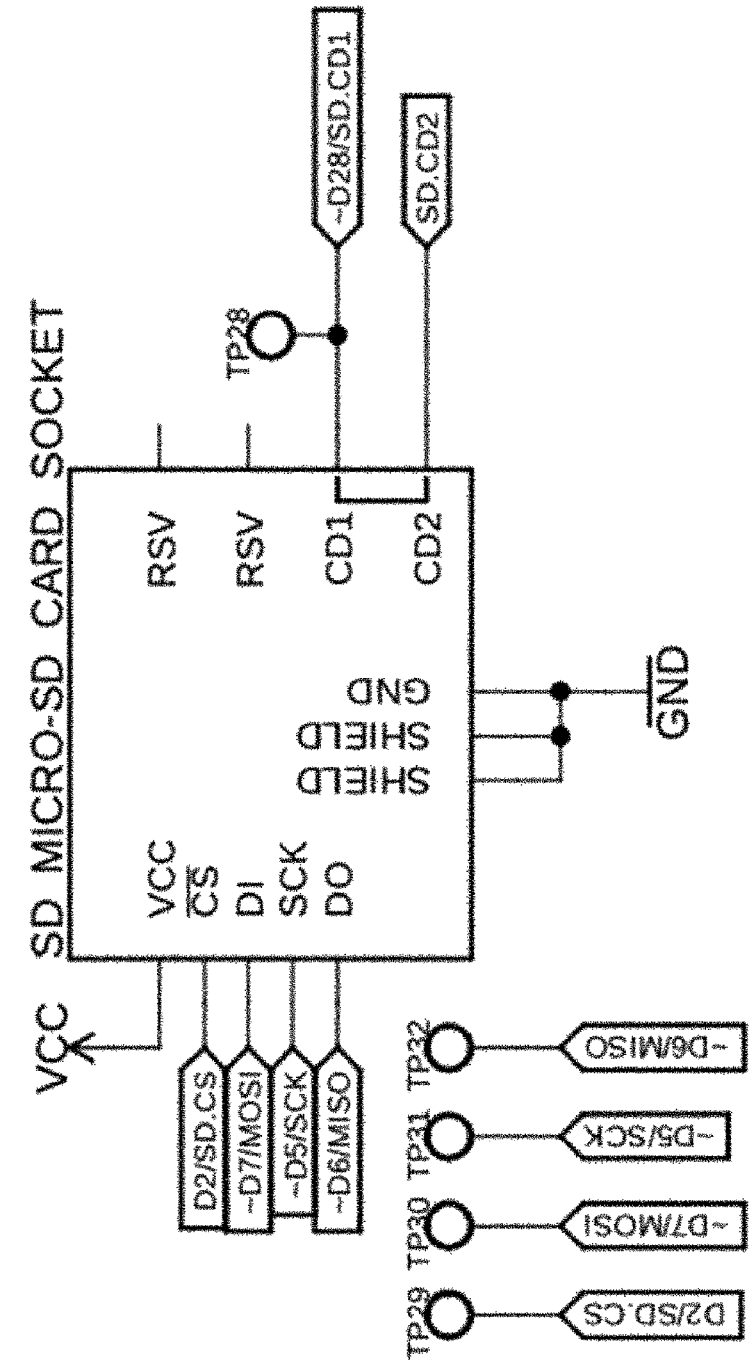
FIG. 21 illustrates a ScanDisk (SD) card.
Figure 22:
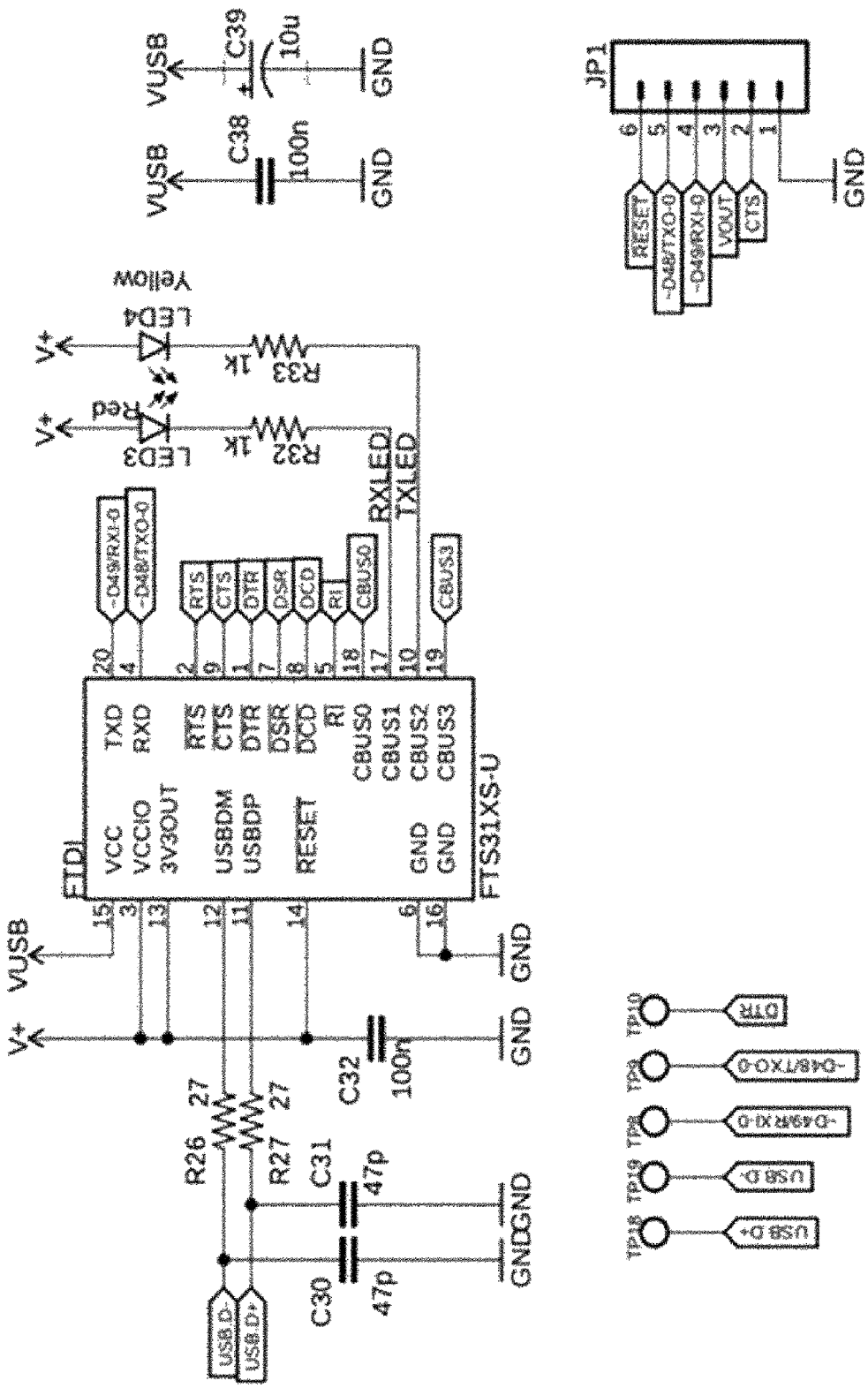
FIG. 22 illustrates a FT231X Serial-to-USB Bridge.

As illustrated in FIG. 9, the central hardware unit 46 comprises the central hardware 46, central enclosure 38, and textile-enclosure harness 58. Connection, connector or adapter are envisioned as replacements for the harness. This central hardware unit 46 supplies power to all hardware, controls the AGMN 42 and the bio-impedance module 44, temporarily stores data, and transmits all data collected in raw, analyzed, encrypted, or other form to the mobile application. The central hardware 46 has several subsystems including an impedance converter 60 and network analyzer (bio-impedance module) 44, active analog filters 62, power management integrated circuits 64, multiplexed digital controls 66, a wireless transmission module 68, an analog to digital converter 70, a microcontroller 72, a peak detector 107, an internal clock 108, an SD card reader 109, a serial-to-USB bridge 110, a heart rate detector and a respiration monitor. The bio-impedance module 44 collects real and complex impedance data by delivering varying current magnitudes of up to 5 mA every 1 kHz across 5 kHz to 100 kHz s to the lower limb 74 and analyzing the delivered signal after it has passed through a section of tissue. A series of multiplexers 66 are utilized so that impedance analysis may be conducted on different segments of tissue by using different textile voltage-sensing electrodes 78 and current-injecting electrodes 80. The current injection 80 and voltage sensing controls 78 result from active filters and multiplexers 76 that allow for different selection of stimulating current magnitude and sensing electrodes. All impedance measurements are taken via the tetrapolar electrode configuration 82 which minimizes the impact of variable skin-electrode contact impedances, polarization effects, and movement artifacts, since the voltage-sensing electrodes draw negligible current. These impedance measurements allow for a robust analysis of body composition of the lower limb, total body composition, swelling progression in the lower limbs, total body fluid retention, and patient compliance to compression therapy. Compliance is defined as when an individual is wearing the compression garment when instructed to by a medical professional. A battery 84 supplies the power required for all these functions and is rechargeable. Instead of a battery 84, a capacitor or other component capable of storing energy and providing power could be used. Instead of providing information on charge of the device to the user, the device could provide that information to any other individual or entity or could omit providing such information. The wireless transmission module 68 relays data to the mobile application 88. Instead of transmitting measured impedance values wirelessly, the device 20 could use a wired connection or other data relay mechanism to transmit measured values. The microcontroller controls all sensors and does minor data analysis.

Instead of utilizing the specific combination of hardware and software components listed here, other hardware and software components that allow for monitoring, transmission, recording, analyzing, or providing feedback on bio-impedance signals could be used. A temperature monitor or array of such monitors are also envisioned.

The central enclosure is a plastic (or other material) container holding the central hardware 46 created by injection molding (or another method). Its primary function is to protect the hardware from damage, for example that caused by abrasion, impact, or water exposure. It has ports to allow the enclosure to be snapped onto or otherwise fastened to the textile-enclosure harness and the hardware to be charged. Instead of a port to charge the device, wireless inductive charging could be utilized. Instead of using charging to power the device, the device could be powered continuously without charging, for example by using a wired plug.

This textile-enclosure harness 58 may both securely fasten the enclosure to the textile layers and allow the enclosure to be removed during garment laundering or for transfer to replacement garments. This harness may facilitate signal transfer between the central hardware/enclosure and the compression garment. This harness may be created by injection molding and may be laminated to the compression garment, stitched to the compression garment, or be held on to the compression garment via a pouch of fabric, among any other joining mechanisms.

The mobile application 88 will receive data from the smart compression garment 36 and will further transmit this data for analysis to an online server. Instead of transmitting data to an application or a server, data could be kept locally on the device 20. Instead of performing data analysis remotely for example in an application or on a server, data analysis could be performed anywhere, for example locally on the device. This mobile application 88 will provide a certain amount of data analysis, display data to the user of the smart compression garment, provide the user with an understanding of the charge of the smart compression garment, and solicit information from the user 22. Instead of providing data and/or feedback through an application, data and/or feedback could be provided directly on the device, for example though an LCD screen. Instead of providing data and/or feedback to the user, the application could provide data and/or feedback to an individual designated by the user 22, a healthcare professional, an insurance company, or any other party with a legitimate interest in the user's healthcare or activity data.

The mobile application 88 is not required if the data-analyzing, data-recording, or feedback-providing functions of the device were incorporated into the device (central hardware unit 46 or similar).

Subjects may wear the WSN 28 while completing five simple and three complex tasks. These tasks may include walking, crawling, lying prone, running, climbing stairs, navigating a 2 ft. diameter cylinder, and turning to the left or right while walking. Additional complex tasks include: rappelling and hand-to-hand combat. The subjects may complete each task repetitively in a variety of environments, both indoors and outdoors, while carrying a variable amount of weight in a backpack. This may ensure data is collected for each task in a variety of terrains and conditions, allowing for robust classification. While the subject is completing these tasks, the WSN 28 may be collecting data from each SU 32 at 200 Hz. Each SU 32 may produce measurements of the x-, y-, and z-accelerations and the relative roll, pitch and yaw from the accelerometer and gyroscope, respectively. Therefore, the WSN 28 may collect 30 points of data per sample, 6 measurements from each of the 5 SUs 32. There may be a minimum of 20,000 samples collected for each task. Each task dataset may be trimmed to an equal number of samples. After all data has been collected for each task, the task datasets may then be labeled and conglomerated via Keras Dataset package.

In preparation for training, the dataset may be shuffled and partitioned into two sections randomly. Two thirds of the data may be used to train the ANN 26 and one third may be used to validate the model. After the completion of this task, the overall model classification accuracy may be obtained along with each task classification accuracy. This methodology was successfully employed to classify simple tasks in the past with only one AGM 48 reading and may likely achieve greater accuracies with the addition of more sensors. In addition, the WSN 28 may investigate whether it is possible to remove data collected from some of the SUs 32 without significantly impacting classification accuracy. This may determine the minimal subset of biomechanical variables that allow the system to achieve the target performance for classifying tasks. This task may take 2 months to complete and may result in a LSTM-DRNN 90 capable of classifying all tasks, both simple and at least one complex, at a minimum of 80% accuracy.

Figure 5B:
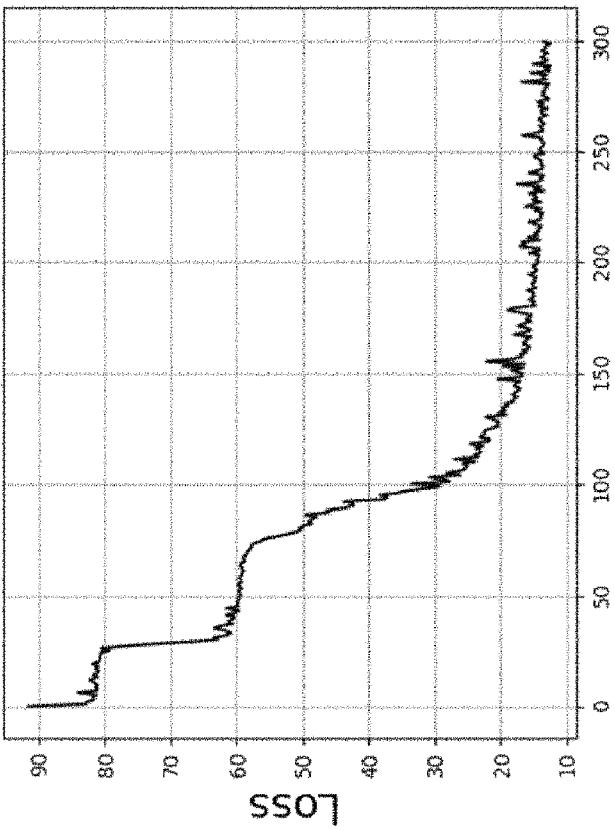
FIG. 5B shows the validation loss of the compression legging system for the artificial neural network (ANN) by training epoch.
Figure 5A:
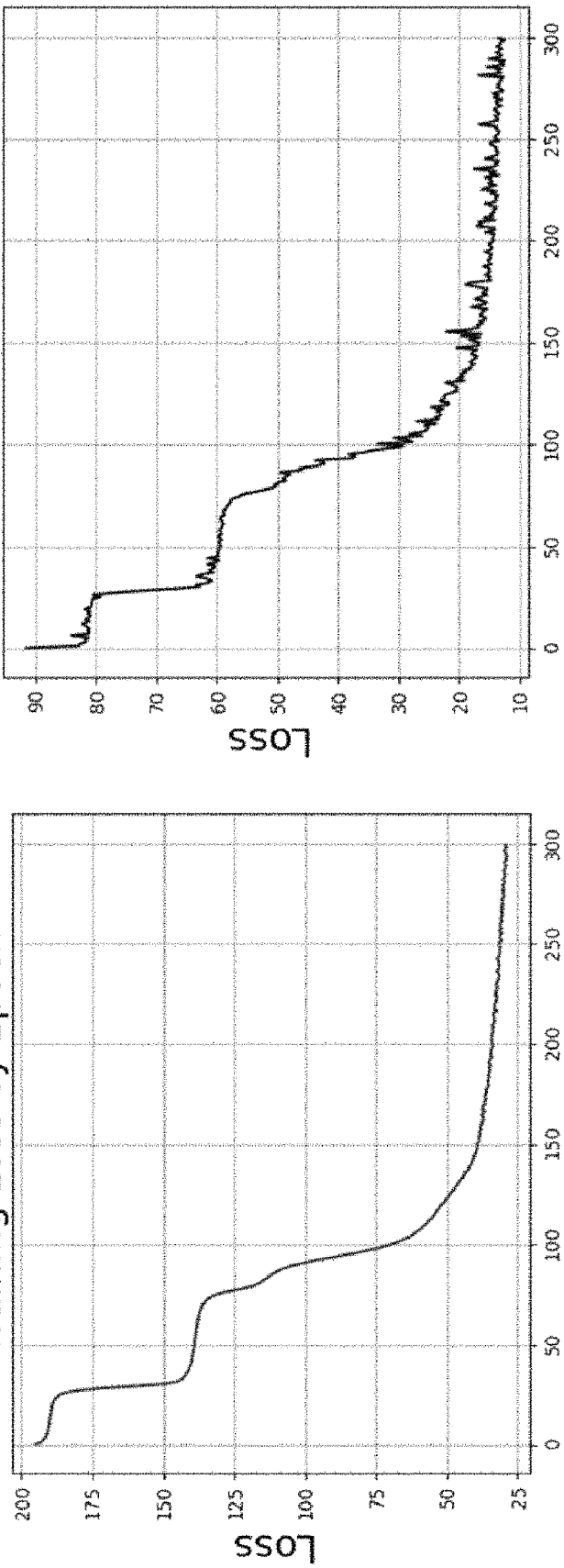
FIG. 5A shows the training loss of the compression legging system for the artificial neural network (ANN) by training epoch.
Figure 6A:
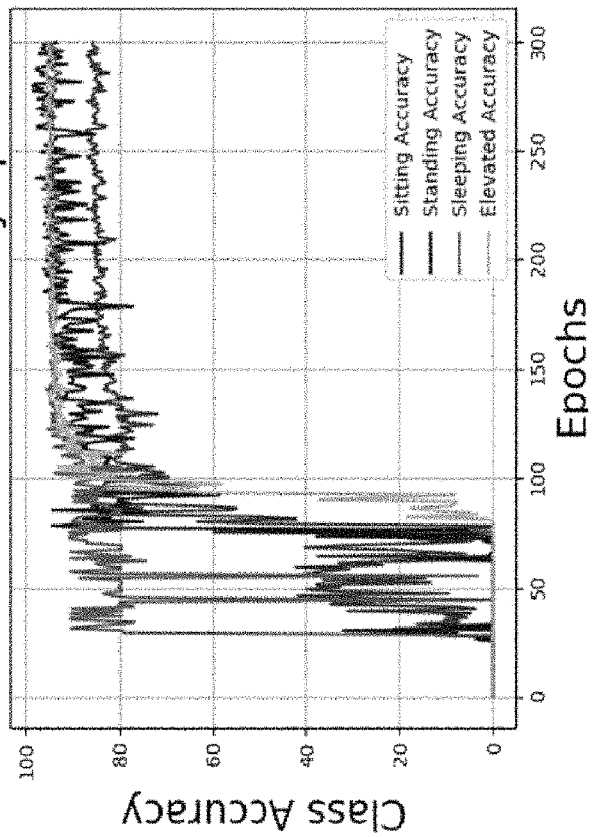
FIG. 6A shows the compression legging system total neural network accuracy by epoch. Accuracy refers to a percent scale (100% accuracy meaning proper detection of task). The compression legging system could determine each of four classes of tasks: sitting, standing, sleeping, and elevating the leg, after training the neural network, with 80-100% accuracy.
Figure 6B:
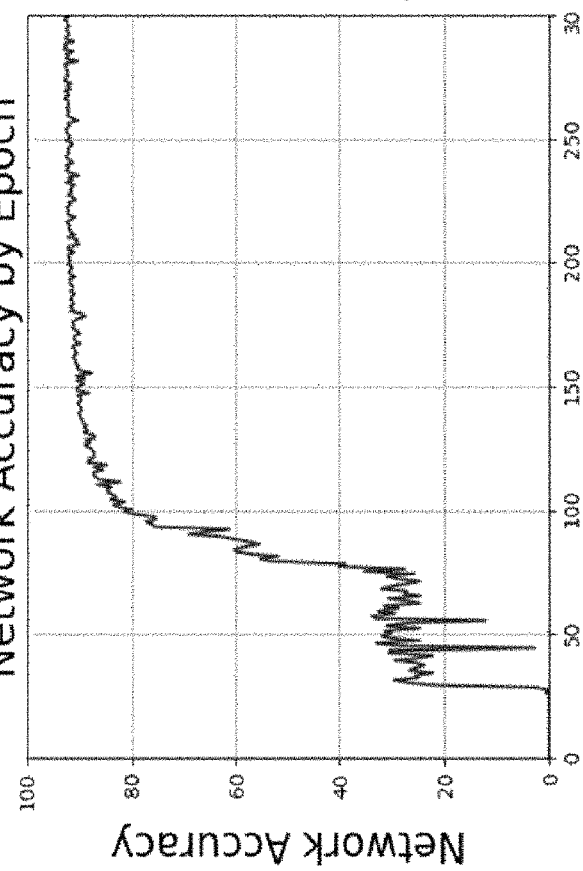
FIG. 6B shows the compression legging system total neural network accuracy and task (class) accuracies by epoch. Accuracy refers to a percent scale (100% accuracy meaning proper detection of task). The compression legging system could determine each of four classes of tasks: sitting, standing, sleeping, and elevating the leg, after training the neural network, with 80-100% accuracy.

This network 34 is a linear neural network 92 with an input layer (6 nodes) 93, 4 hidden layers (75, 150, 450, and 150 nodes) 94, and an output layer (4 nodes) 95. The ANN 26 was initialized using PyTorch packages. A sigmoid function was utilized as the summing function and to introduce non-linearity into the model. The loss function utilized was mean-square loss. The optimizer was stochastic gradient descent. The dataset was partitioned to ensure the data utilized to train the model was not utilized to test and validate the model's accuracies. The ANN 26 was trained over 300 epochs with a batch size of 32 and a learning rate of 0.05 by first training a batch and then validating a batch to approach maximum accuracy. The overall network accuracy was 92.01%. The class accuracies were as follows: sitting: 85.61%, standing: 93.43%, sleeping: 94.42%, and elevating the leg: 95.13%. The validation and training loss may be seen in FIG. 5. Each task accuracy and the overall network accuracy by epoch may be seen in FIG. 6.

It is also possible to monitor the patient's compliance to compression therapy, since the ANN 26 and the BIS 96 system can each detect whether the patient is wearing the device. Furthermore, the ANN's 26 ability to distinguish between leg orientations and postures may allow the system to minimize the confounding effect of such changes on swelling measurement. This monitor may detect immobility and paralysis for the Wells Score (Table 1).

The proposed smart compression legging applies pressure identical to that of a waist-high compression stocking (40 mmHg at ankle, 15 mmHg at upper thigh) 14. The legging may have two layers, each delivering half the required pressure (such pressures are additive). The interior layer may contain the textile electrodes 10, which may be seamlessly knitted into the legging with a circular knitting machine. Such a machine can create a seamless garment from multiple types of fibers, in this case nylon fibers and the silver-coated nylon fibers that may act as the electrodes 10 and signal traces 106. Alternatives to silver coated nylon fibers have been envisioned such as any other conductive fiber. Instead of conductive fiber, any means of reliably relaying a bioimpedance signal from electrodes 10 to central hardware 46, for example wires or wireless electrodes, could be used.

The knitted fabric portions of the compression garment 36 exerts compression to the wearer's extremity. Fabric, cloth, or other wearable material may replace knitted fabric. Compression is provided through a manufacturing process where lycra or other elastic material is woven through the rest of the knitted material in such a way to allow the garment to exert pressure to the wearer when worn. Manufacturing processes other than circular knitting or injection-molding could be used. The relative density of lycra or other elastic material in a section of knitted material correlates to the pressure delivered. Typically, the compression garment is designed such that the pressure it exerts on the wearer gradually increases from a minimum at the most proximal aspect of the extremity covered by the garment to a maximum at the most distal aspect of the extremity covered by the garment. The most distal aspect of the extremity covered by the garment therefore represents the maximum pressure exerted, which is typically about 20 mmHg, about 30 mmHg, or about 40 mmHg. The most proximal aspect of the extremity covered by the garment typically has a corresponding minimum pressure of about 15 mmHg, about 20 mmHg, or about 30 mmHg, respectively. To achieve the optimal pressures, multi-layering of garments may be used. A zipper may be added to the end of the garment which provides the maximal pressure to enable the garment to be donned (put on) and doffed (taken off) easier. Alternatively, a section of non-elastic fabric may replace the most distal aspect of the garment. This non-elastic fabric may utilize a Velcro® flap to exert the desired amount of pressure and may be sewed onto the knitted fabric. The compression is not required to be medical-grade and a compression could be left out for non-medical uses.

The four electronic subcomponents of the compression garment 36 transmit signals between the wearable sensor network 28 and the lower limb 74 of the user 22. These components are textile voltage-sensing electrodes 78, textile current-injecting electrodes 80, textile electronic vias 98, and textile electronic traces 100. In order to incorporate the four electronic subcomponents, the compression garment 36 may have two layers, each delivering half the required compressive pressure (such pressures are additive). Instead of stitched electronic vias 98, seamless knitting, soldering, or any other joining mechanisms could be used to join the signal traces 106 to the electrodes 10.

The interior layer may contain the textile electrodes 10, which may be knitted into the garment 36 with a circular knitting machine or a flat knitting machine. Such machines can create a seamless garment from multiple types of fibers, in this case nylon fibers and the silver-coated nylon fibers that may act as the electrodes, electronic traces, and electronic vias. Circular current-injecting band electrodes 80 lie on the most proximal aspect of the extremity covered by the garment and the most distal aspect of the extremity covered by the garment. These textile current-injecting electrodes 80 are defined as the patches of silver-coated nylon fabric (silver fabric) which transmit current to the extremity for bioimpedance spectroscopy. These electrodes may be fashioned in a circumferential band of silver fabric material 102 on the interior layer of the garment, in a rectangular patch of silver fabric material on the interior layer, or in other configurations. These electrodes must be in contact with the skin to properly function. At least two voltage-sensing electrodes 78 lie on each extremity 104 between each pair of current-injecting band electrodes 78. These textile current-injecting electrodes 78 are defined as the patches of silver-coated nylon fabric which transmit voltages of the extremity for bioimpedance spectroscopy. These electrodes 10 may be fashioned in the same forms as, or in other forms than, the textile current-injecting electrodes 78.

The exterior layer of the garment may contain the silver signal traces 106 connecting the textile electrodes 10 of the interior layer to the central hardware 46 on the lower back 50. Such traces 106 eliminate the need for bulky wires in the legging. These traces 106 are defined as the lines of silver-coated nylon fabric which overlay the textile electrodes 10 in the internal layer of the compression garment 36 and which run to the central hardware 46 of the wearable sensor network 28. These textile traces 106 of the compression garment 36 are connected to traditional circuit elements of the wearable sensor network 28 by soldering conductive fibers from each trace to the hardware, utilizing metal snaps, utilizing ribbon cable connectors, utilizing raised wire connectors, or utilizing other methods.

Manufacture of Compression Legging System:
Step 1: Assembling the Garment Layers 36

The two layers (interior and exterior) may be stitched together for stability, as may the locations where the signal traces 106 and the electrodes 10 touch. These strategies were successfully employed to create FDA-approved ECG electrodes 10 capable of capturing and transferring high-quality signals. Instead of two layers, more or fewer layers of a garment could be utilized to achieve the same results.

Step 2: Assembling the Garment Layers

The interior and exterior layers may be stitched together for mechanical stability, electrical insulation between the skin and electrical textile traces 100, and signal transmission between textile electronic traces 100 and textile electrodes 10. The locations where the signal traces 106 and the electrodes 10 touch may be stitched together to ensure signals may transmit properly between the external and internal layers of the compression garment. These stitches are considered to be the textile electronic vertical interconnect accesses (vias) 98, which are defined as electrical pathways which allow signals to be conducted between layers of the garment.

Step 3: Installing Information Transfer Application

The proposed smart compression legging 36 may be Bluetooth-interfaced or otherwise wirelessly interfaced or interfaced with a wired connection with a mobile application to provide readings to the patient. The back-end of the application may utilize Amazon Web Service's (AWS) security, database and analytics features. AWS is fully equipped to handle patient data, is scalable, and is commonly used in healthcare. Patients with PTS may use the application 88 to detect recurrent DVT and to provide information for the Wells Score (Table 1) including which of their legs is affected by PTS, the presence of collateral superficial veins, scores for pain or tenderness in their leg, the date of a recent surgery, their history of cancer, their history of cast immobilization, and the presence of pitting edema. The patient's primary care physician may aid the patient in this task. Additionally, a questionnaire developed with emergency medicine providers may be utilized to determine if an alternative diagnosis is as likely as DVT (Table 1).

Figure 2:
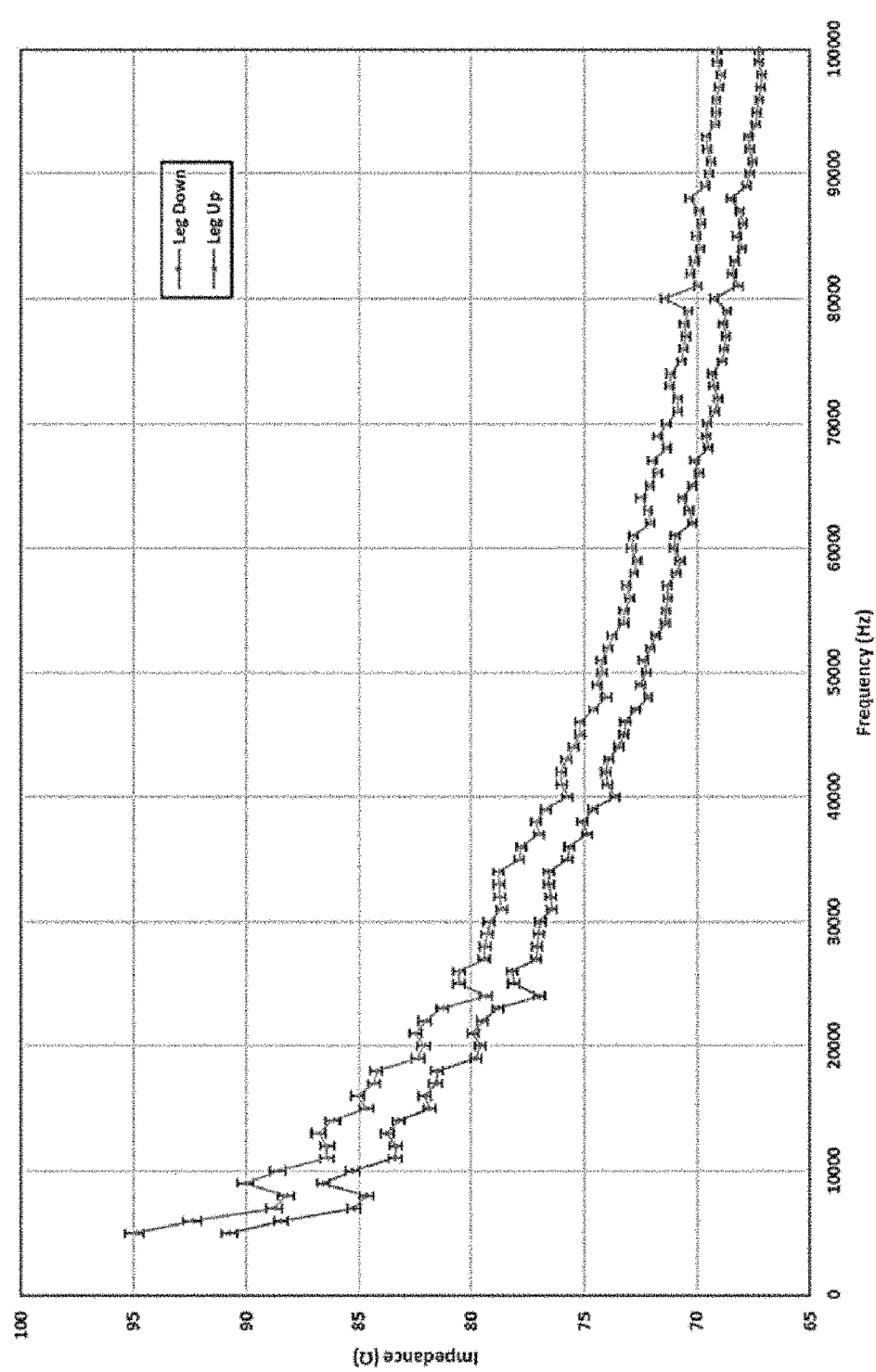
FIG. 2 demonstrates the difference in impedance in the leg due to activity and position. The compression legging system electrodes and hardware could detect and transmit frequency from a human subject while raising and lowering the leg. Points are the mean±95% CI of 12 frequency readings (n=12) in five human subjects (n=5) over a range of frequencies (5,000-100,000 Hz). Statistically significant differences in bio-impedance between leg raised versus leg resting down could be detected in subjects wearing the compression legging system.

Elevating the leg causes fluid to leave the leg due to gravity. This phenomenon was used to validate that the system's current tetrapolar BIS prototype ("alpha prototype") 96 can detect swelling in the leg. Instead of using the tetrapolar electrode configuration 82, any other electrode configuration could be used. FIG. 2 details preliminary studies conducted using the system to demonstrate the performance of its impedance-measuring applications. Subjects (N=5) followed a testing protocol to study the effect of leg position on extracellular fluid changes labeled as 1) "Leg Down" (leg hovering with gravitational vector) and 2) "Leg Up" (leg raised against gravitational vector). The "Leg Down" test was conducted first. During each test, subjects 23 were indicated to remain in the specified position for 2 minutes prior to initiating the multi-frequency bioimpedance analysis. The multi-frequency (5 kHz-100 kHz) bioimpedance analysis was conducted for a total of 2 minutes, where samples were recorded every 30 seconds. Each test was repeated in triplicates with a 1-minute resting period between each reading. In total, there were 4 readings per test, totaling to 12 readings per position study. Data was analyzed to calculate impedance per frequency with a corresponding 95% confidence interval to demonstrate statistical significance per frequency and subject.

More frequencies are envisioned including below 5 kHz and above 100 kHz. Instead of sampling every 1 k Hz, data could be sampled frequently (e.g. every 2 kHz or every 500 Hz or at irregular intervals).

The system was used to conduct a preliminary feasibility study of the ability of an accelerometer-trained artificial neural network (ANN) 26 to differentiate between different leg orientations. A healthy human subject wore the alpha prototype and sat, stood, slept, or elevated the leg while a total of 43,865 acceleration measurements were taken. An ANN 26 was trained with all data samples over 150 epochs. The training and validation loss validated that the network was trained appropriately (i.e. not over or under trained). The ANN 26 successfully distinguished between sitting, standing, sleeping, and elevating the leg over 95% of the time (all class accuracies are >95%), allowing for robust patient activity monitoring.

Figure 3:
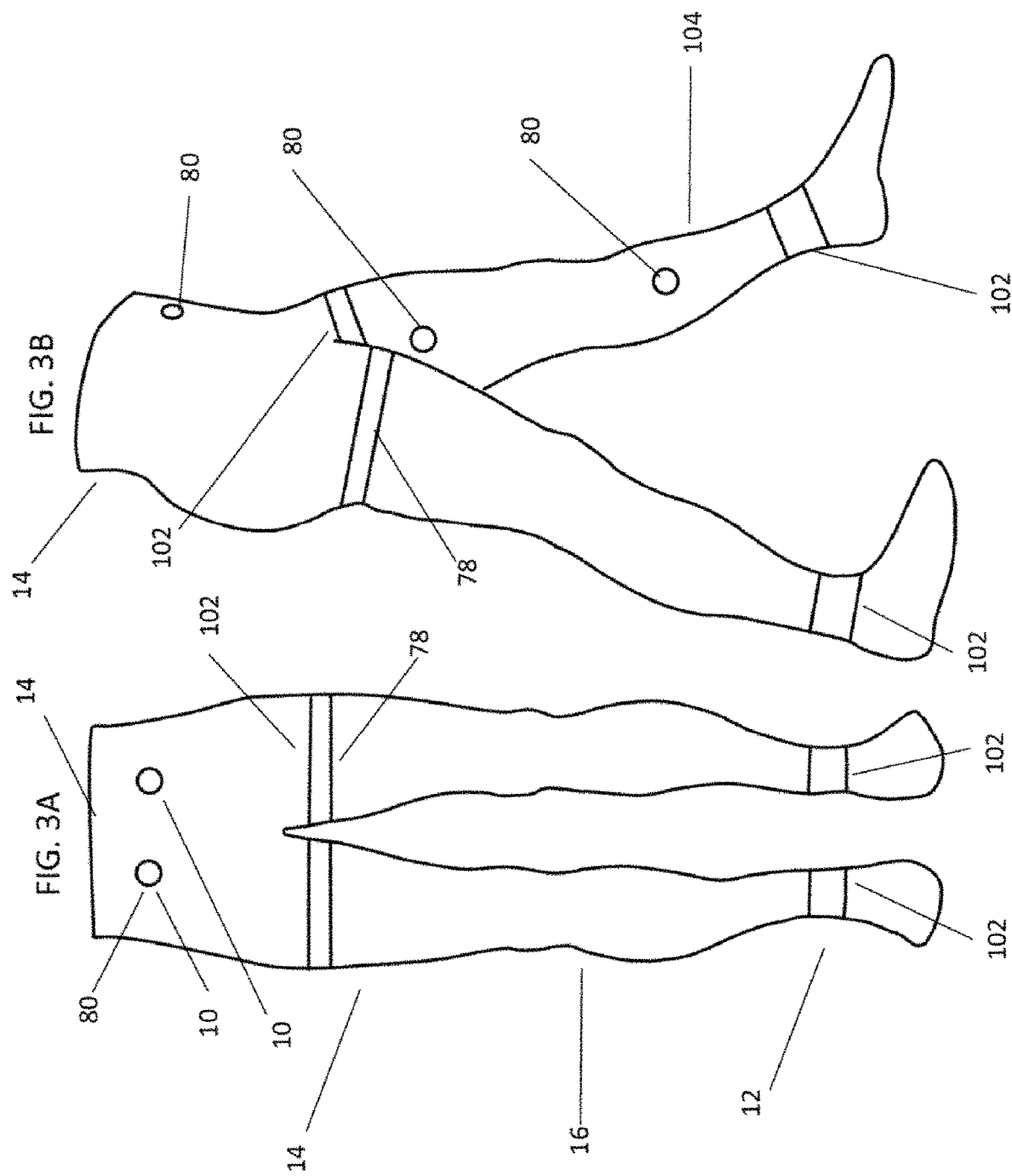
FIG. 3A illustrates a back view of the smart compression legging system that comprises compression material containing the following components: i) compression material with fabric traces, ii) central hardware housing the monitor, iii) current-injecting electrodes, and iv) voltage sensing electrodes. Features of the interior are shown: current-injecting electrodes and voltage sensing electrodes.
FIG. 3B illustrates a side view of the smart compression legging system that comprises compression material containing the following components: i) compression material with fabric traces, ii) central hardware housing the monitor, iii) current-injecting electrodes, and iv) voltage sensing electrodes. Features of the interior are shown: current-injecting electrodes and voltage sensing electrodes.

The system uses fabricated textile voltage-sensing (78 in FIG. 3) 78 and current-injecting electrodes (80 in FIG. 3) 80 for impedance measurement. Voltage-sensing electrodes 78 were constructed from 0.75"×0.75" patches of silver conductive fabric (LessEMF, #A321), while current-injecting electrodes 80 were formed from 0.75" wide, 10"-20" long circular bands of the same fabric. Electrodes 10 were adhered to the interior of a compression garment with fabric glue and interfaced to the rest of the alpha prototype with metal snaps. Snaps were insulated from the skin with electrical tape during testing.

The performance of these electrodes in making BIS 96 measurements with TEC 82 was compared to that of standard FDA-approved adhesive Red Dot™ electrodes (3M, #2560) using the alpha prototype. Four impedance measurements were taken from a healthy human subject at each kHz frequency from 5 kHz to 100 kHz. Six (6) replicates were performed for voltage-sensing electrodes 78 and four (4) replicates for current-injecting electrodes 80. A two sample, two-tailed T-test was conducted at each frequency. Results indicated that the system's textile electrodes gave impedances no statistically significant difference from those obtained with Red Dot™ electrodes at 72% of all frequencies evaluated (alpha=0.05).

Alternative uses of the system have been envisioned including determining ideal fit for a bespoke garment, full body strain measurements, pressure mapping anywhere on the body such as underfoot, pulse monitor (pressure sensors), respiration monitor (transthoracic impedance), monitoring orthopedic health in the leg (detecting synovium swelling changes), cartilage health monitor, muscle activity monitor via the voltage sensing electrodes, EKG monitor in a compression shirt with voltage sensing electrodes, monitoring venous return in anti-gravity straining maneuvers, and monitoring fluid redistributions in mechanical counter-pressure suits.

Figure 7:
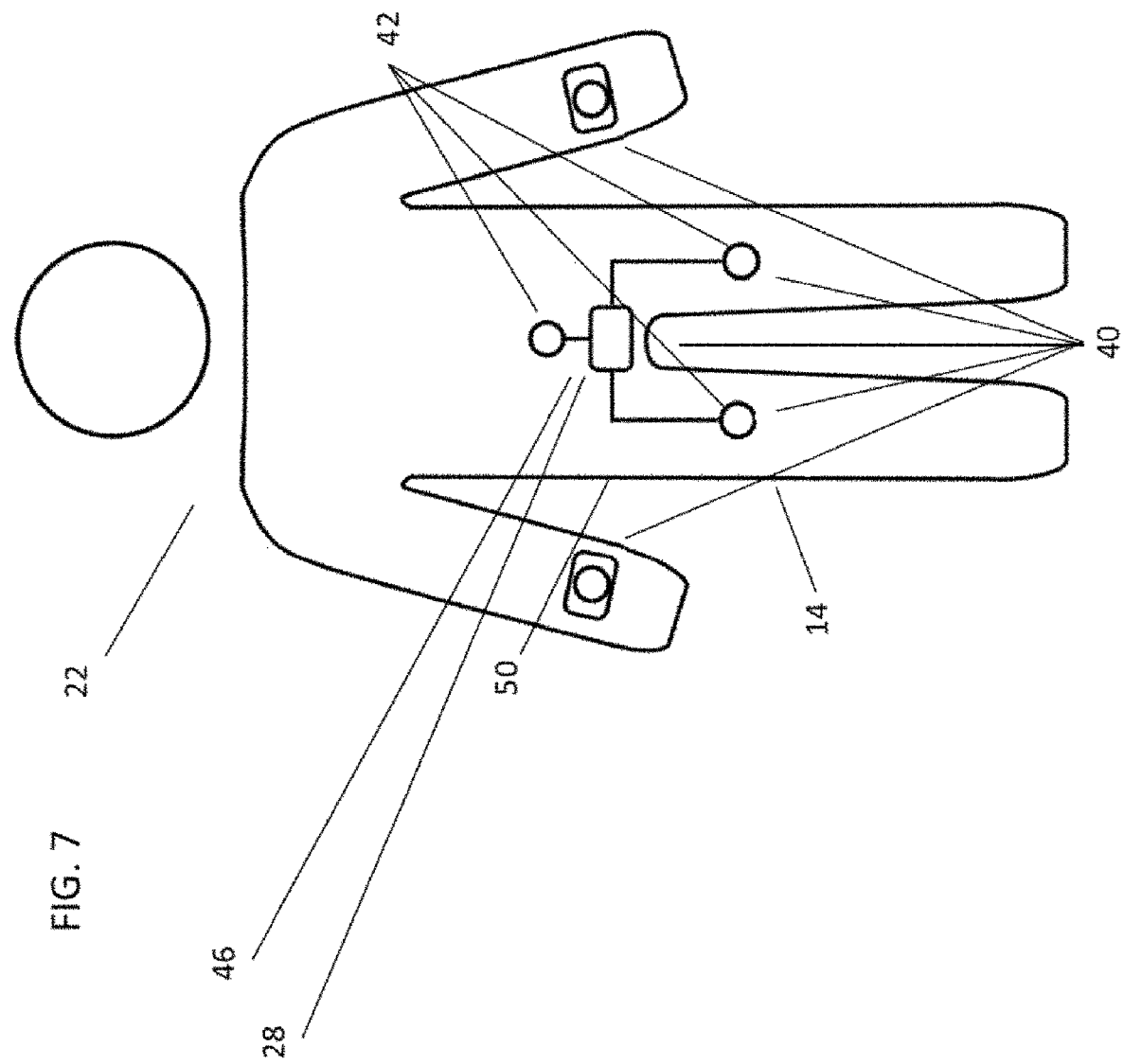
FIG. 7 illustrates a wearable sensor network (WSN) including 5 sensor units (SUs) (circles), 3 microcontroller units (MCUs) (gray squares) and connecting flat wires (lines).
Figure 8:
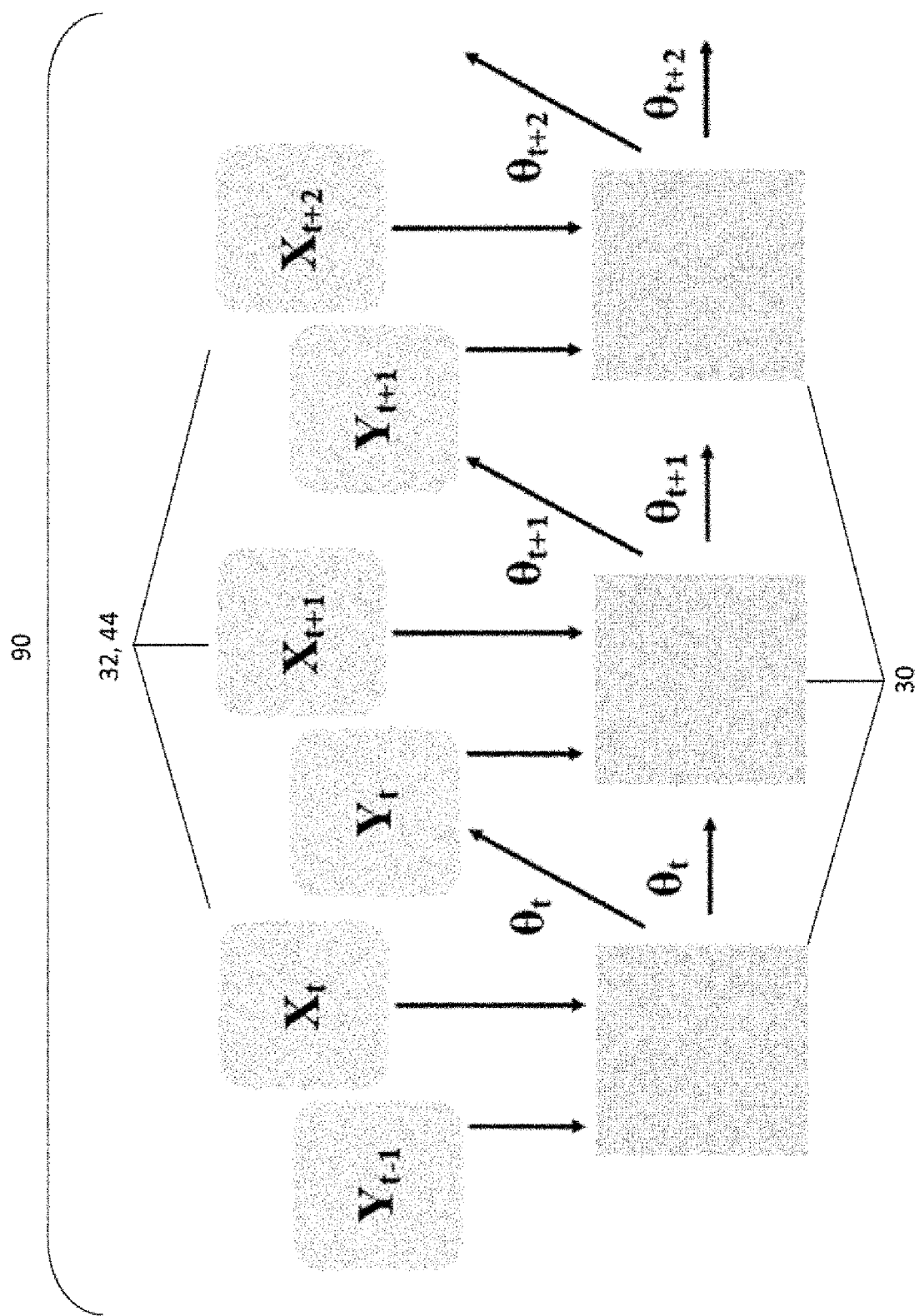
FIG. 8 illustrates the architecture of Long Short-Term Memory Deep ("LSTM") where X represents the bio-impedance inputs from each sensor unit (SU), Y represents the output of the network for a given sample, and the blank box represents the neural network.

A wearable sensor network (WSN) 28 may be constructed to gather biomechanical data. As illustrated in FIG. 7. WSN 28 may include five sensor units (SUs) 32, each containing a single six-axis accelerometer-gyroscope module (AGM) 42. A six-axis AGM 42 is a small electromechanical device that measures static and dynamic acceleration forces. These sensors 42 are highly sensitive and commonly used in missiles, cell phones, and other devices to determine the orientation of the device in three-dimensional space. A microcontroller unit (MCU) 72 may operate each SU 32 and may harvest and save parameters obtained at a 200 Hz sampling rate. Several strategies are envisioned to determine the optimal method to attach the WSN 28 to a subject such as hook and loop fasteners such as Velcro®, embedded sensors, straps, and safety pins.

Optimizations for the WSN 28 may include: the addition of more AGMs 42, the removal of AGMs 42, the addition of other physiological sensors (e.g. electromyograms) and replacing flat wires with Bluetooth communicators. Optimizations for the ANN 28 may include: pre-processing of data to extract features, analyzing acceleration and gyroscope data points separately, and altering the existing architecture.

The WSN 28 may be constructed using commercial off-the-shelf components including existing AGMs 42 and printed circuit boards to ensure the circuit performs as expected. Custom enclosures 38 may be designed and 3D-printed for each SU 32, the MCUs 72 and batteries 84 to reduce impacts, abrasion and dirt from damaging the circuitry. In addition, enclosures 38 may ensure the wiring connecting the SUs 32 on the lower limbs and torso to the MCU 72 on the torso may remain in place during movement.

The anatomical position of the WSN 28 may be seen in FIG. 7. Three SUs 32 containing AGMs 42 may be placed on each proximal posterior thigh of the soldier and the posterior lower back. An MCU 72 may be located on the posterior lower back and may connect to those three SUs 32 via flat wiring. Instead of placing the MCU 72 on the lower back, it could be placed anywhere on the garment such as on the thighs. Instead of a central hardware enclosure on the garment, hardware could be located off the garment and could receive all necessary signals wirelessly. Instead of a single central hardware, the device could be split into several enclosure units to reduce size and minimize ergonomic issues.

Two additional SUs 32 may be located on each wrist. Two MCUs 72 may control each of these SUs 32. The relative position and acceleration of a soldier's center of gravity, upper thighs, and wrists are unique during the execution of a given task, and this configuration has been successfully utilized to classify complex and simple tasks. This task may result in a WSN 28 capable of collecting biomechanical data from a soldier.

The classification model may be utilized to detect blood clot formation in patients suffering from post-thrombotic syndrome (PTS).

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

The invention claimed is:

1. A system for detection of a human disease, wherein the system comprises:
   a compression garment, the compression garment comprising a wearable sensor network and an application;
   the wearable sensor network comprising a plurality of electrodes, wherein four electrodes of the plurality of electrodes are configured to be alternately activated in each leg of a user, wherein the four electrodes are configured to be activated in a configuration sequence consisting of two current-injecting electrodes and two voltage-sensing electrodes a first current injecting electrode, a first voltage sensing electrode, a second voltage sensing electrode, and a second current injecting electrode, respectively; and the wearable sensor network comprising a multiplexor configured to sequentially alternate which two electrodes of the four electrodes are activated as the voltage-sensing electrodes, enabling a data collection and a data analysis from a plurality of different locations of each leg of the user, the collected data comprising bio-impedance measurements of each location of the plurality of different locations of each leg of the user, and each location of the plurality of different locations of each leg of the user positioned between the two voltage-sensing electrodes, wherein the wearable sensor network further comprises a central hardware unit, wherein at least one accelerometer-gyroscope module and at least one bio-impedance module are connected to the central hardware unit by wiring, textile electronic traces, or conductive connections;

the at least one bio-impedance module configured to collect the bio-impedance measurements from each location of the plurality of different locations of each leg of the user positioned between the two voltage-sensing electrodes, and the at least one accelerometer-gyroscope module configured to collect an additional data set from the user, the additional data set comprising acceleration and gyroscopic data from each leg of the user;

wherein the central hardware unit is configured to supply power to the at least one accelerometer-gyroscope module and to the at least one bio-impedance module; to temporarily store the bio-impedance measurements from the bio-impedance module and the additional data set from the at least one accelerometer-gyroscope module; and to transmit the bio-impedance measurements and the additional data set to a mobile application, wherein the mobile application is configured to receive a third data set from additional modules and to further transmit the bio-impedance measurements, the additional data set, and the third data set to an online server;

wherein the bio-impedance module is configured to collect the bio-impedance measurements by delivering a plurality of current signals to each location positioned between the two voltage-sensing electrodes of each leg of the user, the plurality of current signals having varying current magnitudes of up to 5 mA every 1 kHz across 5 kHz to 100 kHz; and wherein the bio-impedance module is further configured to analyze the plurality of delivered current signals after the plurality of delivered current signals have passed through a section of tissue at each location positioned between the two voltage-sensing electrodes of each leg of the user.

2. The system of claim 1, wherein the disease is selected from the group consisting of swelling, inflammation, post-thrombotic syndrome (PTS), deep vein thrombosis (DVT), venous injury, venous stasis (Virchow's triad of hypercoagulability), and pulmonary emboli (PE).

3. The system of claim 1, wherein the compression garment is waist high stockings, knee high stockings, pantyhose, compression sleeve, headband, or any skin-contacting garment.

4. The system of claim 3, wherein the electrode configuration includes a circular current injecting band electrode on each end of the compression garment at the distal and proximal end of the garment.

5. The system of claim 4, wherein the voltage-sensing electrodes lie on the compression garment adjacent to each leg of the user between each pair of current-injecting band electrodes.

6. The system of claim 5, wherein the electrodes are configured to be applied to the skin at a pressure of 15-40 mmHg.

* * * * *